United States Patent
Nielsen et al.

(10) Patent No.: US 11,497,886 B2
(45) Date of Patent: Nov. 15, 2022

(54) INTERMITTENT URINARY CATHETER ASSEMBLY

(71) Applicant: Coloplast A/S, Humlebaek (DK)

(72) Inventors: Henrik Lindenskov Nielsen, Smoerum (DK); Marianne Lund Dalsgaard, Maaloev (DK); Thomas Nesa Gogotic, Hilleroed (DK); Mads Hjaelmsoe Hansen, Smoerum (DK)

(73) Assignee: Coloplast A/S, Humlebaek (DK)

( * ) Notice: Subject to any disclaimer, the term of this patent is extended or adjusted under 35 U.S.C. 154(b) by 26 days.

(21) Appl. No.: 17/261,588

(22) PCT Filed: Jul. 19, 2019

(86) PCT No.: PCT/DK2019/050233
§ 371 (c)(1),
(2) Date: Jan. 20, 2021

(87) PCT Pub. No.: WO2020/015804
PCT Pub. Date: Jan. 23, 2020

(65) Prior Publication Data
US 2021/0290895 A1 Sep. 23, 2021

(30) Foreign Application Priority Data
Jul. 20, 2018 (DK) .......................... PA 2018 70494

(51) Int. Cl.
*A61M 25/00* (2006.01)
*B65D 77/04* (2006.01)
*B65D 81/22* (2006.01)

(52) U.S. Cl.
CPC ........... *A61M 25/002* (2013.01); *B65D 77/04* (2013.01); *B65D 81/22* (2013.01)

(58) Field of Classification Search
CPC ............ A61M 25/002; A61M 25/0017; A61M 27/00; A61M 2210/1078;
(Continued)

(56) References Cited

U.S. PATENT DOCUMENTS

| 761,235 A | 5/1904 | Kepler |
| 1,060,665 A | 5/1913 | Bell |

(Continued)

FOREIGN PATENT DOCUMENTS

| CA | 2904514 A1 | 9/2014 |
| CN | 1106744 A | 8/1995 |

(Continued)

OTHER PUBLICATIONS

Sherman, M. (1998), Medical Device Packaging Handbook, New York.

(Continued)

*Primary Examiner* — Chun Hoi Cheung
(74) *Attorney, Agent, or Firm* — Coloplast Corp., Coloplast A/S; Nick Baumann

(57) ABSTRACT

A urinary catheter assembly is provided. The catheter assembly has a first outer package (20), which contains a second inner package (1). The second inner package includes a hydrophilic coated, intermittent catheter 82) and liquid swelling medium. The first outer package is made of a first material with a WVTR value between 1 and 6 g/(m²·24 h) and the second inner package is made of a second material with a second WVTR value below 3 g/(m²·24 h). An intermediate cavity (25) is defined inside the first outer package, but outside the second inner package. The first and second WVTR-values are balanced in such a way that the relative humidity (RH) is below 90% in the intermediate (Continued)

cavity. This prevents condensation on the inner surface of the first outer package and on the outer surface of the second inner package.

17 Claims, 6 Drawing Sheets

(58) Field of Classification Search
CPC ...... A61M 2210/1089; A61M 25/0111; A61M 2025/0018; A61M 2209/06; B65D 77/04; B65D 81/22; B65D 77/30; B65D 77/32; B65D 77/34; B65D 77/36
USPC ........ 206/210, 438, 364, 571; 604/544, 265, 604/172
See application file for complete search history.

(56) References Cited

U.S. PATENT DOCUMENTS

| | | | |
|---|---|---|---|
| 1,120,549 | A | 12/1914 | Schellberg |
| 2,856,932 | A | 10/1958 | Griffitts |
| 3,154,080 | A | 10/1964 | Rowan et al. |
| 3,321,097 | A | 5/1967 | Solowey |
| 3,421,509 | A | 1/1969 | Fiore |
| 3,444,860 | A | 5/1969 | Harrell |
| 3,648,704 | A | 3/1972 | Jackson |
| 3,683,928 | A | 8/1972 | Kuntz |
| 3,750,875 | A | 8/1973 | Juster |
| 3,762,399 | A | 10/1973 | Riedell |
| 3,794,042 | A | 2/1974 | De Klotz et al. |
| 3,854,483 | A | 12/1974 | Powers |
| 3,894,540 | A | 7/1975 | Bonner, Jr. |
| 3,930,580 | A | 1/1976 | Bazell et al. |
| 3,934,721 | A | 1/1976 | Juster et al. |
| 3,967,728 | A | 7/1976 | Gordon et al. |
| 4,026,296 | A | 5/1977 | Stoy et al. |
| 4,062,363 | A | 12/1977 | Bonner, Jr. |
| 4,140,127 | A | 2/1979 | Cianci et al. |
| 4,170,996 | A | 10/1979 | Wu |
| 4,652,259 | A | 3/1987 | O'Neil |
| 4,692,154 | A | 9/1987 | Singery et al. |
| 4,875,719 | A | 10/1989 | Mylett |
| 5,226,530 | A * | 7/1993 | Golden ............... A61M 25/002 206/364 |
| 5,454,798 | A | 10/1995 | Kubalak et al. |
| 5,645,048 | A | 7/1997 | Brodsky et al. |
| 5,688,459 | A | 11/1997 | Mao et al. |
| 5,895,374 | A | 4/1999 | Roedsten |
| 6,059,107 | A | 5/2000 | Noested et al. |
| 6,065,597 | A | 5/2000 | Pettersson et al. |
| 6,073,759 | A | 6/2000 | Lamborne et al. |
| 6,090,075 | A | 7/2000 | House |
| 6,117,120 | A | 9/2000 | Heininger |
| 6,391,010 | B1 | 5/2002 | Wilcox |
| 6,402,726 | B1 | 6/2002 | Genese |
| 6,544,240 | B1 | 4/2003 | Borodulin et al. |
| 6,578,709 | B1 | 6/2003 | Kavanagh et al. |
| 6,602,244 | B2 | 8/2003 | Kavanagh et al. |
| 6,634,498 | B2 | 10/2003 | Kayeroed et al. |
| 6,899,355 | B2 | 5/2005 | Klein et al. |
| 6,986,868 | B2 | 1/2006 | Madsen |
| 7,311,698 | B2 | 12/2007 | Tanghoj et al. |
| 7,380,658 | B2 * | 6/2008 | Murray .................. B65B 55/22 604/265 |
| 7,886,907 | B2 | 2/2011 | Murray et al. |
| 8,011,505 | B2 | 9/2011 | Murray et al. |
| 8,205,745 | B2 | 6/2012 | Murray et al. |
| 8,523,843 | B2 | 9/2013 | Kavanagh et al. |
| 8,720,685 | B2 | 5/2014 | Murray et al. |
| 8,740,863 | B2 | 6/2014 | Nestenborg et al. |
| 9,028,858 | B2 | 5/2015 | Nielsen et al. |
| 9,072,862 | B2 | 7/2015 | Murray et al. |
| RE47,513 | E | 7/2019 | Murray et al. |
| 10,758,704 | B2 | 9/2020 | Hickmott et al. |

| | | | |
|---|---|---|---|
| 2001/0001443 | A1 | 5/2001 | Kayerod et al. |
| 2002/0144920 | A1 | 10/2002 | Samuels |
| 2002/0193762 | A1 | 12/2002 | Suydam |
| 2003/0060807 | A1 | 3/2003 | Tanghoj et al. |
| 2005/0015076 | A1 | 1/2005 | Giebmeyer et al. |
| 2005/0070882 | A1 | 3/2005 | McBride |
| 2005/0107860 | A1 | 5/2005 | Ignagni et al. |
| 2005/0261664 | A1 | 11/2005 | Rome et al. |
| 2006/0025753 | A1 | 2/2006 | Kubalak et al. |
| 2006/0142737 | A1 | 6/2006 | Tanghoj |
| 2006/0161115 | A1 | 7/2006 | Fangrow |
| 2006/0196783 | A1 | 9/2006 | Bruun et al. |
| 2007/0225687 | A1 | 9/2007 | House |
| 2008/0171992 | A1 | 7/2008 | House |
| 2008/0172016 | A1 | 7/2008 | House |
| 2009/0208368 | A1 | 8/2009 | Waldrep et al. |
| 2011/0114520 | A1 | 5/2011 | Matthison-Hansen |
| 2011/0120892 | A1 | 5/2011 | Frederiksen et al. |
| 2011/0160704 | A1 | 6/2011 | Park |
| 2011/0172491 | A1 | 7/2011 | Piskun et al. |
| 2011/0230864 | A1 | 9/2011 | House |
| 2011/0295239 | A1 | 12/2011 | Gustavsson |
| 2012/0165790 | A1 | 6/2012 | Gustavsson et al. |
| 2012/0271282 | A1 | 10/2012 | Schertiger et al. |
| 2012/0316515 | A1 | 12/2012 | Terry |
| 2013/0161208 | A1 | 6/2013 | Gustavsson |
| 2013/0165867 | A1 | 6/2013 | Isaacson et al. |
| 2013/0186778 | A1 | 7/2013 | Terry |
| 2013/0261607 | A1 | 10/2013 | Nielsen |
| 2013/0261608 | A1 | 10/2013 | Tanghoj |
| 2013/0292286 | A1 | 11/2013 | Van Groningen et al. |
| 2013/0327664 | A1 | 12/2013 | Tanghoj |
| 2014/0262859 | A1 | 9/2014 | Knapp et al. |
| 2015/0068927 | A1 | 3/2015 | Mcburney et al. |
| 2015/0112314 | A1 | 4/2015 | Gustavsson et al. |
| 2015/0133898 | A1 | 5/2015 | Murray et al. |
| 2015/0173937 | A1 | 6/2015 | Jackson |
| 2015/0250656 | A1 | 9/2015 | Maksimow |
| 2015/0258305 | A1 | 9/2015 | Dye |
| 2015/0265801 | A1 | 9/2015 | Rostami |
| 2015/0306342 | A1 | 10/2015 | Rostami et al. |
| 2016/0015929 | A1 | 1/2016 | Tanghoej et al. |
| 2016/0038713 | A1 | 2/2016 | Kearns et al. |
| 2016/0038717 | A1 | 2/2016 | Murray et al. |
| 2016/0193447 | A1 | 7/2016 | Matthiassen |
| 2017/0000978 | A1 | 1/2017 | Murray et al. |
| 2017/0203910 | A1 | 7/2017 | Buse et al. |
| 2017/0216557 | A1 | 8/2017 | Kearns et al. |
| 2020/0222659 | A1 | 7/2020 | Schertiger et al. |
| 2021/0290895 | A1 | 9/2021 | Nielsen et al. |

FOREIGN PATENT DOCUMENTS

| | | |
|---|---|---|
| CN | 2347608 Y | 11/1999 |
| CN | 1537024 A | 10/2004 |
| CN | 1718940 A | 1/2006 |
| CN | 1795024 A | 6/2006 |
| CN | 101132826 A | 2/2008 |
| CN | 102654224 A | 9/2012 |
| CN | 102892452 A | 1/2013 |
| CN | 103127597 A | 6/2013 |
| CN | 103301551 A | 9/2013 |
| CN | 103791132 A | 5/2014 |
| CN | 103945893 A | 7/2014 |
| CN | 104379210 A | 2/2015 |
| CN | 204840604 U | 12/2015 |
| DE | 2227416 A1 | 12/1972 |
| DE | 2511198 A1 | 9/1975 |
| DE | 2458217 A1 | 6/1976 |
| DE | 10213411 A1 | 10/2003 |
| DE | 10334372 A1 | 2/2005 |
| DE | 102009031447 A1 | 1/2011 |
| EP | 0166998 A2 | 1/1986 |
| EP | 0217771 A1 | 4/1987 |
| EP | 0679506 A1 | 11/1995 |
| EP | 1018323 A1 | 7/2000 |
| EP | 0923398 B1 | 11/2001 |
| EP | 2072075 A1 | 6/2009 |
| EP | 1312385 B2 | 10/2009 |

(56) References Cited

FOREIGN PATENT DOCUMENTS

| | | | |
|---|---|---|---|
| EP | 2423125 A1 | 2/2012 |
| EP | 2423126 A1 | 2/2012 |
| EP | 2423127 A1 | 2/2012 |
| EP | 2695636 A1 | 2/2014 |
| EP | 3210909 A1 | 8/2017 |
| EP | 3392167 A1 | 10/2018 |
| GB | 322426 A | 12/1929 |
| GB | 2007507 A1 | 5/1979 |
| JP | 2001139059 A2 | 5/2001 |
| JP | 2007533331 A | 11/2007 |
| JP | 2009279456 A | 12/2009 |
| JP | 5512265 B1 | 6/2014 |
| RU | 2012129843 A | 1/2014 |
| RU | 2013130998 A | 1/2015 |
| RU | 2013131785 A | 1/2015 |
| RU | 2584649 C2 | 5/2016 |
| RU | 2598811 C2 | 9/2016 |
| WO | 9204932 A1 | 4/1992 |
| WO | 9406377 A1 | 3/1994 |
| WO | 9416747 A1 | 8/1994 |
| WO | 199630277 A1 | 10/1996 |
| WO | 199726937 A1 | 7/1997 |
| WO | 199747349 A1 | 12/1997 |
| WO | 9806642 A1 | 2/1998 |
| WO | 199811932 A1 | 3/1998 |
| WO | 9819729 A1 | 5/1998 |
| WO | 0030696 A1 | 6/2000 |
| WO | 200030575 A1 | 6/2000 |
| WO | 200047494 A1 | 8/2000 |
| WO | 0152763 A1 | 7/2001 |
| WO | 2003002178 A2 | 1/2003 |
| WO | 03092779 A1 | 11/2003 |
| WO | 2004050155 A1 | 6/2004 |
| WO | 2005004964 A1 | 1/2005 |
| WO | 2005004970 A1 | 1/2005 |
| WO | 2005014055 A2 | 2/2005 |
| WO | 2007022223 A2 | 2/2007 |
| WO | 2007106431 A2 | 9/2007 |
| WO | 2007146820 A2 | 12/2007 |
| WO | 08146836 A1 | 12/2008 |
| WO | 2010006620 A1 | 1/2010 |
| WO | 11000353 A1 | 1/2011 |
| WO | 2011079129 A1 | 6/2011 |
| WO | 2011109393 A1 | 9/2011 |
| WO | 2012016570 A2 | 2/2012 |
| WO | 2012016571 A2 | 2/2012 |
| WO | 2013049733 A2 | 4/2013 |
| WO | 2015142506 A1 | 9/2015 |
| WO | 15184365 A1 | 12/2015 |
| WO | 2016206701 A1 | 12/2016 |
| WO | 2018059637 A1 | 4/2018 |
| WO | 2020015804 A1 | 1/2020 |

OTHER PUBLICATIONS

Hanafy el al., Ancient Egyptian Medicine, Urology, vol. IV, No. 1, 1974.
Macey et al., The evolution and development of the urinary catheter, Aust. N.Z. J. Surg., vol. 63, 1993.

* cited by examiner

INTERMITTENT URINARY CATHETER ASSEMBLY

The disclosure relates to an intermittent urinary catheter assembly.

BACKGROUND

Users of intermittent catheters may have become incontinent due to a spinal cord injury, a disease such as multiple schlerosis or spina bifida or other factors resulting in the user losing control of the bladder function. Many users also have poor hand dexterity as a result of their condition.

An intermittent urinary catheter is used 4-6 times a day for intermittently draining the bladder of a user. During each emptying, the intermittent urinary catheter sits in urethra for 10-15 minutes or less. Such a catheter has an ability to slide easily through the urethra without exposing the urethral walls to any risk of damage. One way of doing this is by imparting an extremely low friction character to at least the part of the surface of the catheter which is introduced into the urethra. The low friction surface character is obtained by incorporating onto the relevant part of the catheter a hydrophilic coating and exposing this coating to contact with a swelling medium prior to use.

SUMMARY OF THE INVENTION

Embodiments relate to a urinary catheter assembly comprising a first outer package of a first material, where the first material has a first water vapour transmission rate (WVTR) determined according to ASTM F1249 at a relative humidity of 90% and a temperature of 38° C. between 1 g/(m²·24 h) and 6 g/(m²·24 h). The first outer package contains a second inner package of a second material, and the second material has a second water vapour transmission rate (WVTR) determined as described below at a relative humidity of 65% RH and a temperature of 30° C. below 3 g/(m²·24 h). An intermediate cavity is defined as an area inside the first outer package and outside the second inner package. The second inner package defines an enclosure, which contains an intermittent urinary catheter with a hydrophilic coating and a swelling medium. The first water vapour transmission rate and the second water vapour transmission rate are balanced in such a way that the RH value is below 90% in the intermediate cavity

BRIEF DESCRIPTION OF THE DRAWING

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
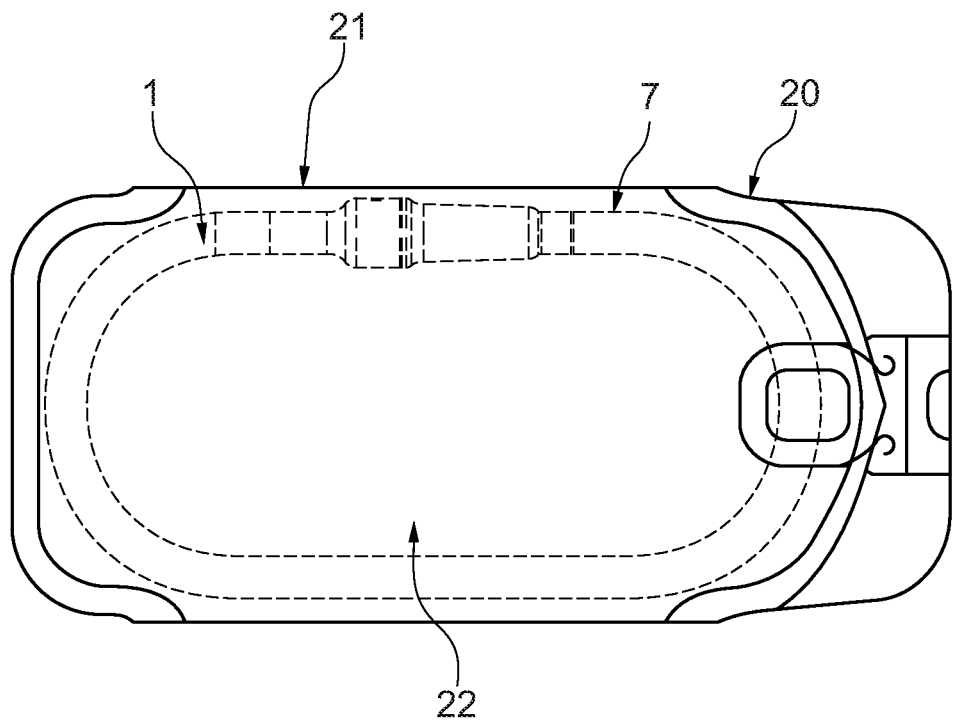
FIGS. 1 and 2 illustrate schematic drawings of urinary catheter assemblies as described

Embodiments relate to a urinary catheter assembly comprising a first outer package of a first material, the first outer package contains a second inner package of a second material, an intermediate cavity defined as area inside the first outer package and outside the second inner package, the second inner package defining an enclosure, the enclosure containing an intermittent urinary catheter with a hydrophilic coating and a swelling medium, wherein the permeability of the first outer package and the permeability of the second inner package is balanced in such a way that the RH value is 100% inside the inner package and the RH value is below 90% in the intermediate cavity.

Embodiments relate to a urinary catheter assembly comprising a first outer package of a first material, the first material having a first water vapour transmission rate (WVTR) determined according to ASTM F1249 at 90% RH and 38° C. between 1 g/(m²·24 h) and 6 g/(m²·24 h), the first outer package contains a second inner package of a second material, the second material having a second water vapour transmission rate (WVTR) measured as described below at 65% RH and 30° C. below 3 g/(m²·24 h);

an intermediate cavity defined as an area inside the first outer package and outside the second inner package, the second inner package defining an enclosure, the enclosure containing an intermittent urinary catheter with a hydrophilic coating and a swelling medium;

wherein the first water vapour transmission rate and the second water vapour transmission rate are balanced in such a way that the RH value is below 90% in the intermediate cavity and wherein the second inner package is made of a multilayer film material comprising layers of Polyethylene (PE) and layers of Styrene-IsoButylene-Styrene (SIBS) and/or layers of combinations of PE and SIBS.

Embodiments further relate to a urinary catheter assembly comprising a first outer package of a first material, the first material having a first water vapour transmission rate (WVTR), the first outer package contains a second inner package of a second material, the second material having a second water vapour transmission rate (WVTR);

an intermediate cavity defined as an area inside the first outer package and outside the second inner package, the second inner package defining an enclosure, the enclosure containing an intermittent urinary catheter with a hydrophilic coating, and a swelling medium;

wherein the relationship between the first and second water vapour transmissions are such that they fulfil the following equations:

$$BF(\text{outer}) = WVTR(\text{outer}) \cdot A(\text{outer}) \cdot p(\text{outer})$$

$$BF(\text{inner}) = WVTR(\text{inner}) \cdot A(\text{inner}) \cdot p(\text{inner})$$

$$RH(\text{cavity}) = RH(\text{storage}) + (100 - RH(\text{storage})) \cdot \frac{1}{\frac{BF(\text{outer})}{\frac{1}{BF(\text{outer})} + \frac{1}{BF(\text{inner})}}} < 90\%;$$

wherein BF(outer) is the barrier flow through the first outer package given in g/24 h, BF(inner) is the barrier flow through the second inner package given in g/24 h, WVTR (outer) is the first water vapour transmission rate and WVTR (inner) is the second water vapour transmission rate, A(outer) is the surface area of the first outer package, A(inner) is the surface area of the second inner package, p(outer) is the difference in RH-value between the ambience and the intermediate cavity (i.e. across the first outer package), and p(inner) is the difference in RH-value between the second inner package and the intermediate cavity (i.e. across the second inner package). RH(cavity) is the RH-value in the intermediate cavity and RH(storage) is the RH-value at the storage location external to the first outer package.

Urinary catheter assemblies as disclosed here are provided with a first outer package with a first permeability and a second inner package with a second permeability, where the permeability may be defined by using the water vapour permeability (WVTR) determined as described below. This method provides a value for the WVTR at 65% RH and 30° C. Other possibilities for determining WVTR exists; in this disclosure also determining WVTR according to ASTM F1249 at 90% RH and 38° C. is used. By ASTM F1249 is meant herein ASTM F1249-13.

By balancing the first and second WVTR values of the first outer package and the second inner package as mentioned above, a urinary catheter assembly having an inner package which is dry on an outer surface is obtained, thereby allowing the second inner package to be easily handled by a user. This is because any liquid inside the outer package but outside the inner package will diffuse out of the assembly through the outer package within a short period of time, such as 1 day or shorter. The diffusion is obtained by having the level of RH inside the outer package and outside the inner package below 90%. The catheter assembly will thus have a balanced loss of swelling medium over time. However, the loss of swelling medium is always so low that the intermittent urinary catheter is fully hydrated during the storage period.

By selecting the first outer package to have the above-mentioned permeability (the first WVTR values), an outer package of a softer, less rigid material can be achieved. By softer and less rigid is meant that the material does not crinkle and make a noise, when touched, and that the edges of the material are less sharp and thereby less prone to chafe the user handling the first outer package. Furthermore, the outer package may be made without an aluminium-layer and will therefore be more environmentally friendly.

In the following, whenever referring to a proximal end of an element of the intermittent urinary catheter assemblies, the referral is to the end adapted for insertion. Whenever referring to the distal end of an element, the referral is to the end opposite the insertion end. In other words, the proximal end is the end closest to the user, when the intermittent urinary catheter is to be inserted and the distal end is the opposite end—the end furthest away from the user when the urinary catheter is to be inserted. The same definitions apply to the second inner package.

The intermittent urinary catheter comprises a main tubular part extending from the distal end to the proximal end. The tip portion is positioned at a proximal end of the catheter and comprises an eyelet part with eyelets and a proximal part proximal of the eyelet part. The proximal part may comprise a proximal rounded closed end of the tubular part. The eyelets serve the purpose of letting urine enter into the inner lumen of the tube. The tip portion may be a Nelaton tip, where the proximal end is simply closed off providing a half-spherical closed end. The tip portion may be integrally moulded with the main tubular part—either as 1 component or 2 component moulding—or it may be provided as a separate element and then attached to the main tubular part, e.g. by welding or adhering. The tip portion may also be made by modifying the main tubular part, i.e. by punching the eyelets and rounding the proximal end to close it off.

The urinary catheter may be made of a polyurethane material (PU) or polyvinyl chloride (PVC) or poly-olefins such as a polyethylene (PE).

Usually urinary catheters used as intermittent urinary catheters are from size 8 FR to size 16 FR. FR (or French size or Charriere (Ch)) is a standard gauge for catheters approximately corresponding to the outer circumference in mm. More accurately, the outer diameter of the catheter in mm corresponds to FR divided by 3. Thus 8 FR corresponds to a catheter with an outer diameter of 2.7 mm and 16 FR corresponds to a catheter with an outer diameter of 5.3 mm.

The intermittent urinary catheters may prior to use be provided with a hydrophilic coating so as to impart a low-friction insertion.

The hydrophilic coating may be provided only on the insertable part of the catheter. The hydrophilic surface coating is of the kind which, when hydrated or swelled using a swelling medium, reduces the friction on the surface area of the catheter which is intended to be inserted into the urinary channel of a user corresponding to the insertable part of the catheter.

An intermittent hydrophilic catheter differs from an indwelling catheter in that the hydrophilic surface coating of such a catheter is not suitable for indwelling use, because the surface coating tends to stick inside the mucosa of the urethra if left inside the body for a period exceeding 5-20 minutes, due to the hydrophilic coating transforming from being highly lubricious when fully wetted (95% weight water) to being adhesive when the hydration level of the coating is reduced (<75% weight water). Furthermore, intermittent implies repeated and short term use, which means that a user of intermittent catheters has to insert a catheter 4 to 6 times a day and leave them sitting in the urethra for a short period (<20 minutes) only. It is therefore an advantage if an intermittent catheter has a very (extremely) lubricious surface with low-friction properties. Moreover, for an intermittent catheter, the insertion of the catheter has to be simple and easy to handle, even for users with low hand-dexterity.

The urinary catheter assembly comprises a medium for activating the hydrophilic surface coating of the catheter. The activating medium is a water based substance, such as sterile water, saline-solution, or any water based liquid.

The storage period of an assembly as above is typically at least 1 year, but may be longer such as 2 or 3 years.

In the intermittent urinary catheter assemblies described here, the swelling medium is in direct contact with the coating during the storage period. This means that the swelling medium is contained inside the second inner package in contact with the hydrophilic coating of the intermittent urinary catheter during the storage period.

For the purpose of this disclosure a film-material is defined as a material having a thickness of below 200 µm. The thickness of the film-material may influence the ability of the second inner package to function as an insertion aid. Embodiments relate to film-materials having a thickness of below 150 µm.

This disclosure mentions an intermediate cavity, which is defined as the area or volume between the first outer package and the second inner package.

A collapse-force as mentioned in this disclosure is the force used to collapse the second inner package enclosing the intermittent urinary catheter, in case the second inner package is used as an insertion aid. In this case, the second inner package will be made as tubular element of film material and will have a maximum diameter of the tubular element of around 10 mm, so that the enclosure inside the second inner package narrowly surrounds the intermittent urinary catheter. The collapse-force is defined as the force used to collapse a narrowly surrounding second inner package in such a way that 30 cm of a male catheter is exposed from a distal eyelet in the insertion tip end. Tests have shown that if the collapse-force for exposing 30 cm of a male catheter is below 6 N, then users will find it easy to collapse the second inner package. This is particularly advantageous for users having poor hand dexterity. In the case that the male catheter has a length of approximately 40 cm, the tubular element of film material may have a length, in a fully extended state, of approximately 34 cm. In this case the collapse-force is measured when the tubular element has collapsed from a fully extended length of approximately 34 cm to a collapsed length of approximately 4 cm. Accordingly, the tubular element is collapsed to a length which is approximately 12% of the fully extended length.

Embodiments relate to a first outer package being made of a film-material with a thickness below 200 µm. The first outer package may be made of a multilayer film-material.

Embodiments relate to a first outer package of film-material that is welded along the edges. In areas, where the package is contemplated to be opened, the welding may be adapted for this purpose, e.g. by a peel-welding technique.

Embodiments relate to the second inner package being of tubular form and providing a close-fit about the catheter. Embodiments relate to the second inner package having a diameter of 15 mm, but may be less such as 12 mm or 10 mm or even 9 mm. This is to be correlated to the diameter of the catheter, which is typically between 2.7 mm and 6 mm. Thus, embodiments provide for a volume inside the second inner package (i.e. the volume of the enclosure), which is large enough to contain the catheter as well as the required swelling medium. The amount of swelling medium may be between 5 and 20 ml such as around 15 ml or 16 ml.

Embodiments relate to an intermittent urinary catheter assembly as above, wherein the second inner package comprises a handle slidingly disposed on the intermittent urinary catheter and a collapsible and flexible tubular film element, which is attached to the handle and which is configured to cover the intermittent urinary catheter from an outlet to an insertion tip in an extended configuration. The tubular film element is attached to a connector at the outlet. The connector and handle are configured to be attached to each other in a detachable manner, so that when the connector and handle are attached to each other, the intermittent urinary catheter is encapsulated completely inside an enclosure provided by the second inner package comprising the tubular film element, the handle and the connector.

By being configured to cover the urinary catheter from the outlet to the insertion tip is meant that the tubular film element covers a majority of the longitudinal extent of the intermittent urinary catheter in an extended configuration. By a majority is meant that the second inner package covers more than 90% of the length of the intermittent urinary catheter from the connector towards the tip in the longitudinal direction, such as more than 95% or 97% of the length. The connector and handle are typically attached to each other in a storage condition, and in that storage condition, the intermittent urinary catheter is encapsulated completely inside the enclosure provided by the second inner package. In a use condition or extended configuration of the assembly, the connector and handle are detached from each other and, typically, the liquid will be drained out from the cavity. The storage condition may also be known as the closed configuration of the second inner package and the use condition may be known as the open configuration of the second inner package.

One advantage of the embodiment is that the second inner package provides a complete enclosure for the intermittent urinary catheter, so that in the storage condition, the sterility is not compromised in any way—even as the second inner package with the intermittent urinary catheter inside the storage cavity is removed from first outer package. The user may drop the second inner package on the floor or even into the toilet, without compromising the sterility of the intermittent urinary catheter itself. In particular, the insertion tip is protected from being contaminated by contact with anything unclean as long as the connector is connected to the handle. Furthermore, when the intermittent urinary catheter is to be used, the user simply detaches the connector from the handle. Following unfolding or unrolling of the tubular film element of the second inner package with the intermittent urinary catheter inside, the intermittent urinary catheter is ready to be used. The second inner package further provides the user with the possibility of gripping and holding the urinary catheter so that it is easier to use. Thereby, the catheter itself can be made of a softer and more bendable material than a catheter that is to be inserted in a straight position.

In an assembly as described above, the user of the assembly only has to handle one item. Users of intermittent urinary catheter assemblies may have reduced hand dexterity making it difficult for them to handle several items. Therefore, it is an advantage that no extra items (e.g. caps or closures) need to be handled. Furthermore, when the connector and handle are separated, each of these two parts provides an intuitive location for handling the catheter, which can be done without compromising the sterility of any part of the catheter.

Embodiments relate to the second inner package being closed with a first closure in the proximal end. Embodiments relate to the second inner package being closed with a second closure in the distal end. Embodiments relate to the first closure being a plug. Embodiments relate to the second closure being a plug. Embodiments relate to the first closure being a peel-welded closure. Embodiments relate to the second closure being a peel-welded closure.

A material suitable for the first outer package is a multilayer film material including Polyethylene (PE).

Embodiments relate to a first outer package being made of a multiple layer film material of a laminate of Polyethylene terephthalate (PETP) and Polyethylene (PE).

Embodiments relate to a first outer package being made of a multiple layer film-material of a laminate of PETP and PE.

Embodiments relate to a second inner package made of a multilayer film material comprising layers of PE and layers of Styrene-IsoButylene-Styrene (SIBS). The multilayer film material may also comprise layers with a combination of PE and SIBS.

In an embodiment, the material of the second inner package is a 5 layer film-material comprising a SIBS layer in the middle, which on each side is covered by a layer made of PE and SIBS and where the outer layers are made of PE.

Including SIBS in the material of the second inner package has the advantage of providing a good impermeability (a low second WVTR value) in combination with a low collapse-force.

Embodiments relate to a second inner package made of a film material of Polyethylene. Polyethylene may be used if the film material is thicker than 50 µm. Polyethylene in thinner material may not have the desired permeability.

Embodiments relate to a first outer package made of a multiple layer film material of a laminate of Polyethylene terephthalate (PETP) and Polyethylene (PE) and a second inner package made of a 5 layer film-material comprising a SIBS layer in the middle, which on each side is covered by a layer made of PE and SIBS and where the outer layers are made of PE Embodiments relate to a first outer package made of a multiple layer film material of a laminate of Polyethylene terephthalate (PETP) and Polyethylene (PE) and a second inner package made of Polyethylene thicker than 50 µm.

Embodiments relate to a first outer package made of a multiple layer film material of a laminate of Polyethylene terephthalate (PETP) and Polyethylene (PE) and a second inner package made of a 5 layer film-material comprising a SIBS layer in the middle, which on each side is covered by further SIBS layers and where the outer layers are made of PE.

Embodiments relate to the intermittent urinary catheter being a male-catheter meaning that the length of the catheter exceeds 30 cm.

Embodiments relate to an intermittent urinary catheter assembly as above, wherein the second inner package is useable as an insertion aid. The second inner package thus comprises a tubular film element, which is easily collapsible to an extent where at least 30 cm from the proximal end of a male catheter can be exposed without noticeable resistance.

In embodiments, the collapse-force used to compress the second inner package to the extent where at least 30 cm is exposed is below 6 N. Thereby users having poor hand dexterity will find it unproblematic to collapse the second inner package 30 cm. In embodiments, the collapse-force used to compress the second inner package to the extent where at least 30 cm is exposed is below 3 N. Having a collapse-force below 3 N provides for a very easily collapsible second inner package and thereby an assembly that is very easy to use for users having dexterity problems.

It is an advantage to provide a second inner package which, on the one hand, is collapsible in the manner described above, thereby allowing it to be easily used as an insertion aid, even for user having dexterity problems, and which on the other hand has a sufficiently low water vapour transmission rate to ensure a required shelf life of the assembly. Furthermore, the water vapour transmission rate of the first outer package should be sufficiently high to ensure that water vapour entering the intermediate cavity through the second inner package diffuses out of the assembly, through the first outer package, within a short period of time, thereby ensuring that the outer surface of the second inner package remains dry, thereby allowing it to be easily handled by the user.

In an embodiment, the tip portion is a flex tip. In this type of embodiment, the tip portion of the intermittent urinary catheter comprises, from the distal end of the tip portion, an eyelet part with eyelets for letting urine into the inner lumen of the catheter, an intermediate part, where the catheter diameter is decreased with respect to the diameter of the remaining part of the catheter, and a proximal part having a bulb with a diameter close to or exceeding the diameter of the tubular part of the catheter. The bulb may also have a diameter that is slightly less than the diameter of the tubular part of the catheter. The bulb may be close to spherical in shape or may be slightly elongated and shaped as an olive or droplet. This type of tip portion may be useful for male users to guide the catheter around the bend in the urethra at the prostate.

In embodiments, where the second inner package includes a handle attachable to the connector, this second inner package allows the tip portion to be protected inside the connector without being bend. A flexible tip portion is adapted to bend easily—and because of the visco-elasticity of the material, the tip portion will have a tendency to deform permanently into a curved position if being subjected to bending for a prolonged period of time. This means that such a bend in the tip portion may be difficult, if not impossible to straighten out again, when the catheter is to be used. Thereby, the catheter will be difficult to insert during the straight part of the urethra.

The eyelets will influence the bending stiffness of the catheter in such a way that the eyelet part will have a reduced bending stiffness compared to the main tubular part of the catheter. The intermediate part may have a diameter that is decreased to such an extent that the bending stiffness of this part is between 60% and 80% of the bending stiffness of the main tubular part of the catheter. This reduced diameter and resulting reduced bending stiffness assist in preventing the catheter from kinking at the eyelets, because the deflection of the catheter will be more evenly distributed, when the intermediate part of the catheter is less rigid (has a lower bending stiffness) than the eyelet part.

In an embodiment, when the intermittent urinary catheter is straightened out, the second inner package does not completely cover the insertion tip, but up to 10 mm of the tip portion projects beyond the proximal end of the handle. In other words, a major portion of the catheter is covered by the second inner package. This has the effect that the proximal end of the tip portion is immediately visible and accessible for insertion into the urethra, whereas the eyelet part with the eyelets will still be positioned inside the handle. Having the eyelets inside the protection of the handle is an advantage, because the catheter is more likely to kink at the eyelets than at other cross-sections along the length of the catheter. So the user can initiate insertion of the intermittent urinary catheter into the urethra and still support the eyelet part of the urinary catheter by squeezing the handle into contact with this part.

Embodiments relate to a urinary catheter assembly comprising a first outer package as described above and a second inner package as described earlier and being provided in an annular closed-loop configuration contained inside the first outer package. In these embodiments, the volume of the first outer package has to be large enough to contain the closed-loop configuration of the second inner package. This large volume influences the level of the first WVTR value, which should be selected in the lower end of the range mentioned above, i.e. between 1 g/(m$^2$·24 h) and 3 g/(m$^2$·24 h). As an example of a first outer package of this type is a first outer package having a surface area of approximately 37000 mm$^2$.

Embodiments relate to a urinary catheter assembly comprising a first outer package as described above and a second inner package as described earlier and being provided in rolled-up configuration with two convolutions. In these embodiments, the volume of the first outer package may be reduced compared to other embodiments. This reduced volume influences the level of the first WVTR value, which may then be selected in the higher end of the range mentioned above, i.e. between 4 g/(m$^2$·24 h) and 6 g/(m$^2$·24 h). As an example of a first outer package of this type is a first outer package having a surface area of approximately 20500 mm$^2$.

DETAILED DESCRIPTION OF THE DRAWING

Embodiments, and features of the various exemplary embodiments described in this application, may be combined with each other ("mixed and matched"), unless specifically noted otherwise.

FIG. 1 illustrates a schematic view of a urinary catheter assembly with a second inner package 1 packed and stored in a first outer package 20. In this embodiment, the first outer package 20 is made of film-material welded along the edges to provide an enclosure 21 in which, the intermittent urinary catheter (not visible) including the tubular film element 7 is stored during storage. The intermediate cavity 22 is the area or volume inside the first outer package 20 but outside the second inner package 1. In this storage configuration, the first outer package has to have a volume large enough to contain the second inner package in a simple, annular closed configuration.

Figure 2:
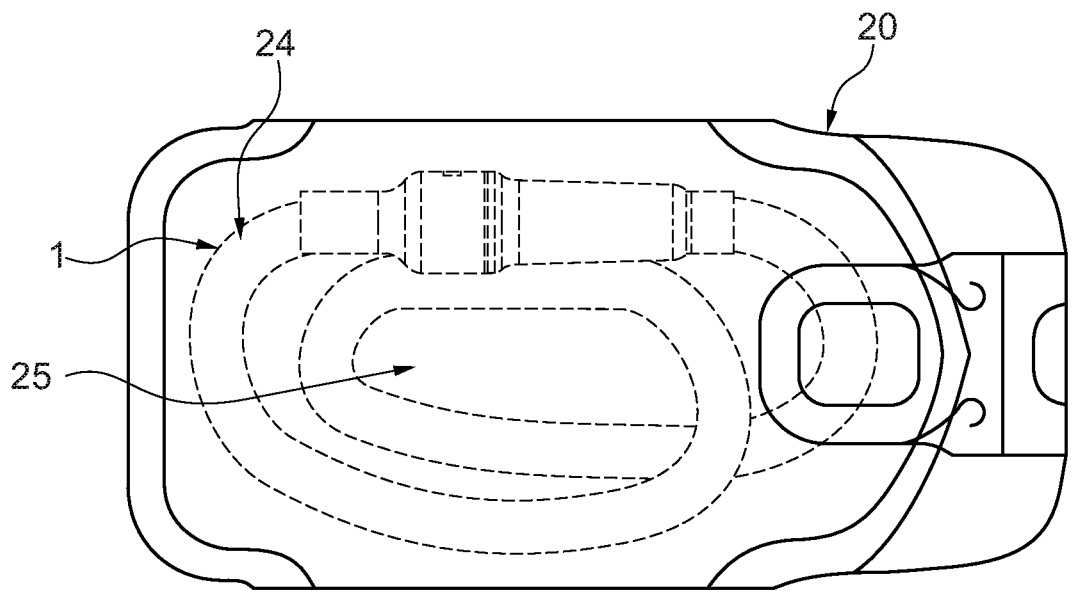

FIG. 2 illustrates a schematic view of another storage configuration of a urinary catheter assembly. The second inner package 1 is in this configuration rolled-up in in two convolutions inside the first outer package 20. In this storage configuration, the first outer package 20 can have a reduced volume compared to FIG. 1, because the second inner package 1 is rolled-up into two convolutions. The second inner package 1 provides an enclosure 24 for the urinary catheter. The intermediate cavity 25 outside of the second inner package 1 and inside the first outer package 20 is also illustrated.

Figure 3:
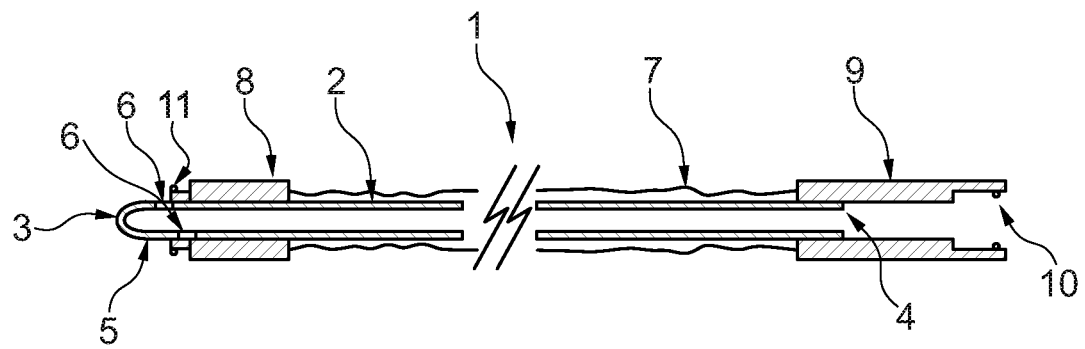
FIGS. 3 to 5 illustrate cross-sectional views of a second inner package FIG. 6 illustrate a cross-sectional view of a part of a second inner package FIG. 7 illustrate a cross-sectional view of a layered structure of a material useful in a second inner package FIG. 8 illustrate a perspective view of a second inner package in a ready for insertion state

FIG. 3 illustrates a cross-sectional view of an embodiment of a second inner package 1 of a urinary catheter assembly, when it is ready to be used. The second inner package 1 includes an intermittent urinary catheter 2, extending from a proximal insertion end 3 to a distal end comprising an outlet 4. The proximal end 3 includes a tip portion 5 with eyelets 6 for letting urine enter into the catheter. The second inner package 1 further includes a tubular film element 7 extending between a handle 8 and a connector 9. The tubular film element 7 is collapsible as the handle 8 is slid along the catheter 2, e.g. during insertion. The connector 9 includes a first snap-fit means 10 configured to cooperate with a complementary second snap-fit means 11 on the handle. The second snap-fit means 11 may be in the form of a resilient flange configured for snapping behind a first snap-fit means in form of a flange 10 on the connector.

Figure 4:
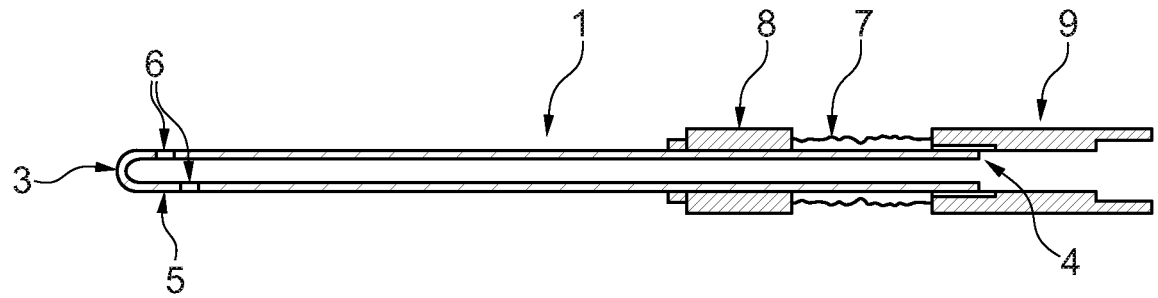

FIG. 4 illustrates a cross-sectional view a second inner package 1 in a collapsed configuration, that is when the intermittent urinary catheter is inserted into the urethra. In use, the user grips the handle 8 and pull the tubular film element 7 backwards over the intermittent catheter in the direction of the connector 9. The tubular film element 7 of the second inner package 1 is collapsible to an extent to only provide limited resistance to being collapsed in front of the connector, as it is described elsewhere in this disclosure, i.e. it has a low collapse-force, e.g. below 6 N or even below 3 N. The figure also illustrates the eyelets 6 in the tip portion 5 in the proximal end 3 of the intermittent urinary catheter.

Figure 5:
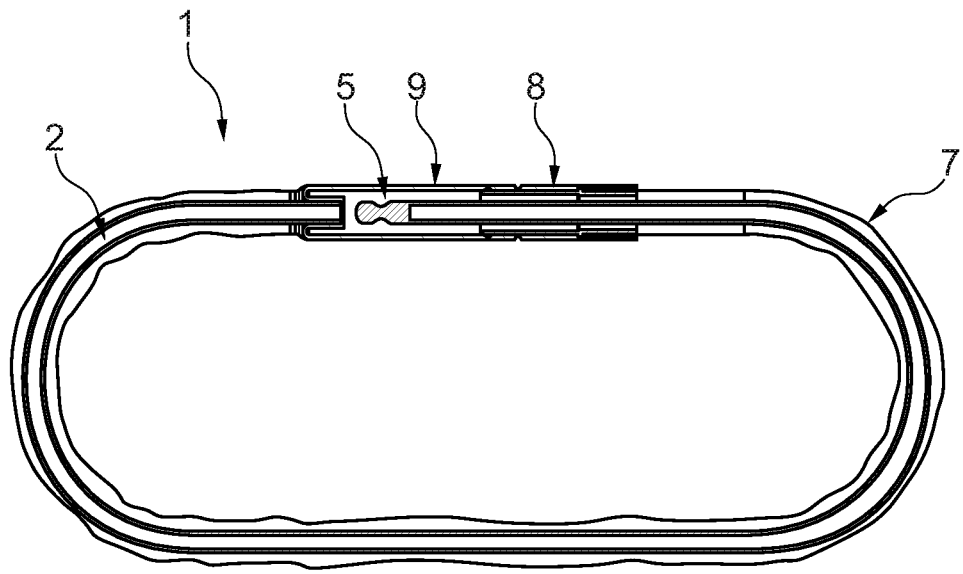

FIG. 5 illustrates a cross-sectional view of a second inner package 1 in a storage condition. When stored, the connector 9 is attached to the handle 8 and the intermittent urinary catheter 2 is thus completely enclosed or encapsulated in the enclosure provided by the tubular film element 7, connector 9 and handle 8. The tip portion 5 is illustrated as being protected inside the connector 9 and handle 8 during storage.

Figure 6:
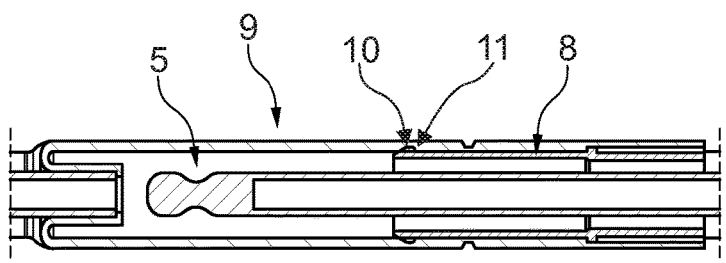

FIG. 6 illustrates a detail of the attachment between the connector 9 and the handle 8. FIG. 6 illustrates how the handle 8 and connector 9 are attached to each other to provide a closed connection and provide a protective cavity for the tip portion 5. The first and second snap-fit means 10 and 11 are also illustrated in FIG. 6.

Figure 7:
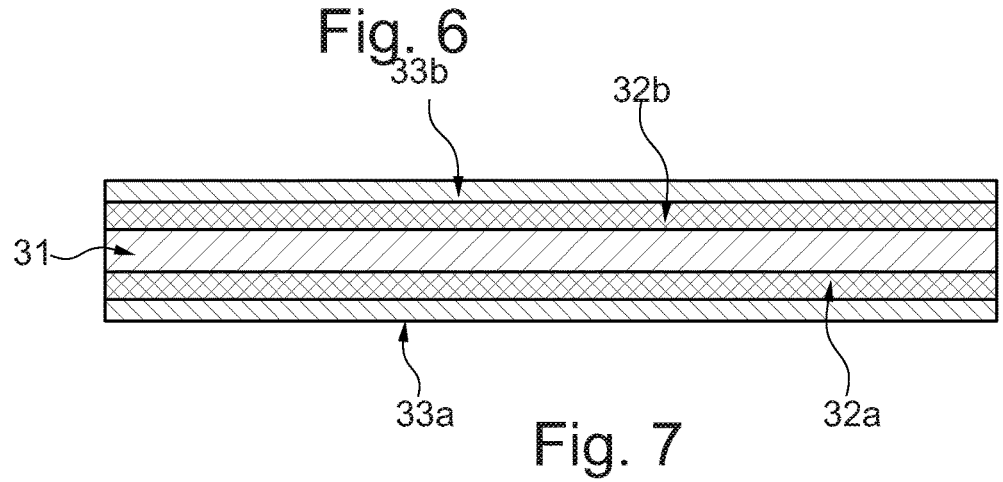

FIG. 7 illustrates a layered structure 30 of a material suitable for use as a second inner package. Starting from the middle, the layer 31, is a SIBS layer. This is on each side covered by a layer 32a and 32b, which is a combination of SIBS and PE. The outermost layers, 33a, 33b are made of PE.

Figure 8:
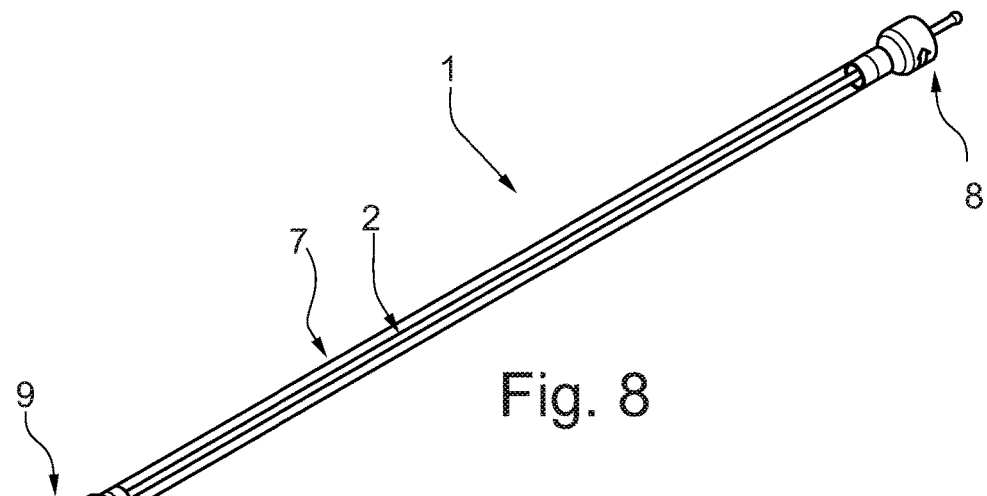

FIG. 8 illustrates a second inner package 1 when it is ready to be used with the handle 8 and connector 9 separated from each other and the intermittent urinary catheter ready for insertion. The tubular film element 7 can be seen as covering the intermittent urinary catheter 2 for a majority of the entire length.

Figure 14:
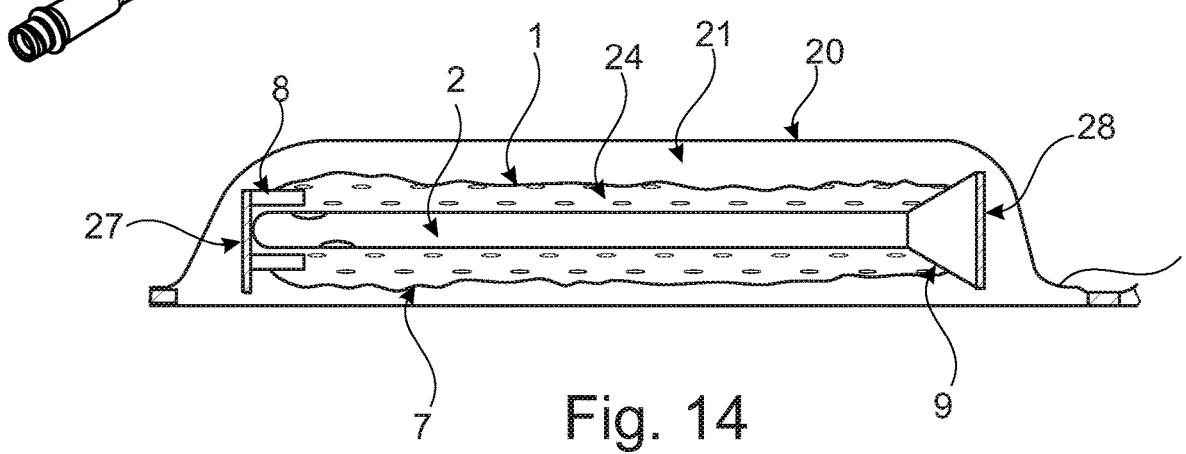
FIG. 14 illustrates a cross-sectional view of a urinary catheter assembly with a second inner package packed and stored in a first outer package.

FIG. 14 illustrates a cross-sectional view of a urinary catheter assembly with a second inner package 1 packed and stored in a first outer package 20. Like with the embodiment of FIGS. 1 and 2, the first outer package 20 is made of film-material welded along the edges to provide an enclosure 21 in which, the intermittent urinary catheter 2 including the second inner package 1 in the form of a collapsible and flexible tubular film element 7 is stored during storage. The collapsible tubular film material 7 is attached to a handle 8 in the proximal end and to a connector 9 in the distal end. The handle 8 is closed with a first closure 27 and the connector is closed with a second closure 28. The first and second closures 27, 28 and the flexible and collapsible tubular film material 7 provide an enclosure 24 for the intermittent urinary catheter 2.

Figure 9A:
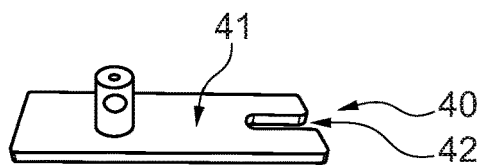
FIGS. 9A and 9B illustrate upper and lower fixtures for use in testing of collapse-force
Figure 9B:
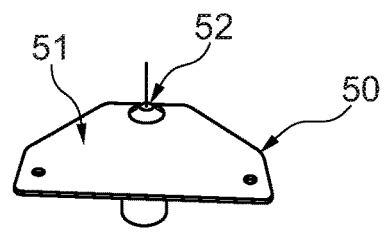

FIGS. 9A and 9B illustrate upper (FIG. 9A) and lower (FIG. 9B) fixtures for use in testing collapse-force of the second inner package. The upper fixture 40 includes an upper plate 41 with a recess 42, which is adapted to let the catheter pass unhindered through it, but which will provide a hold-down for a handle on the second inner package. The lower fixture 50 includes a lower plate 51 with a hold 52 adapted for connecting a connector on the catheter or the second inner package. The hold 52 will typically be a cylindrical element with a steering pin standing up from the lower plate 51—typically perpendicular to the lower plate 51.

Figures 10A, 10B, 10C:
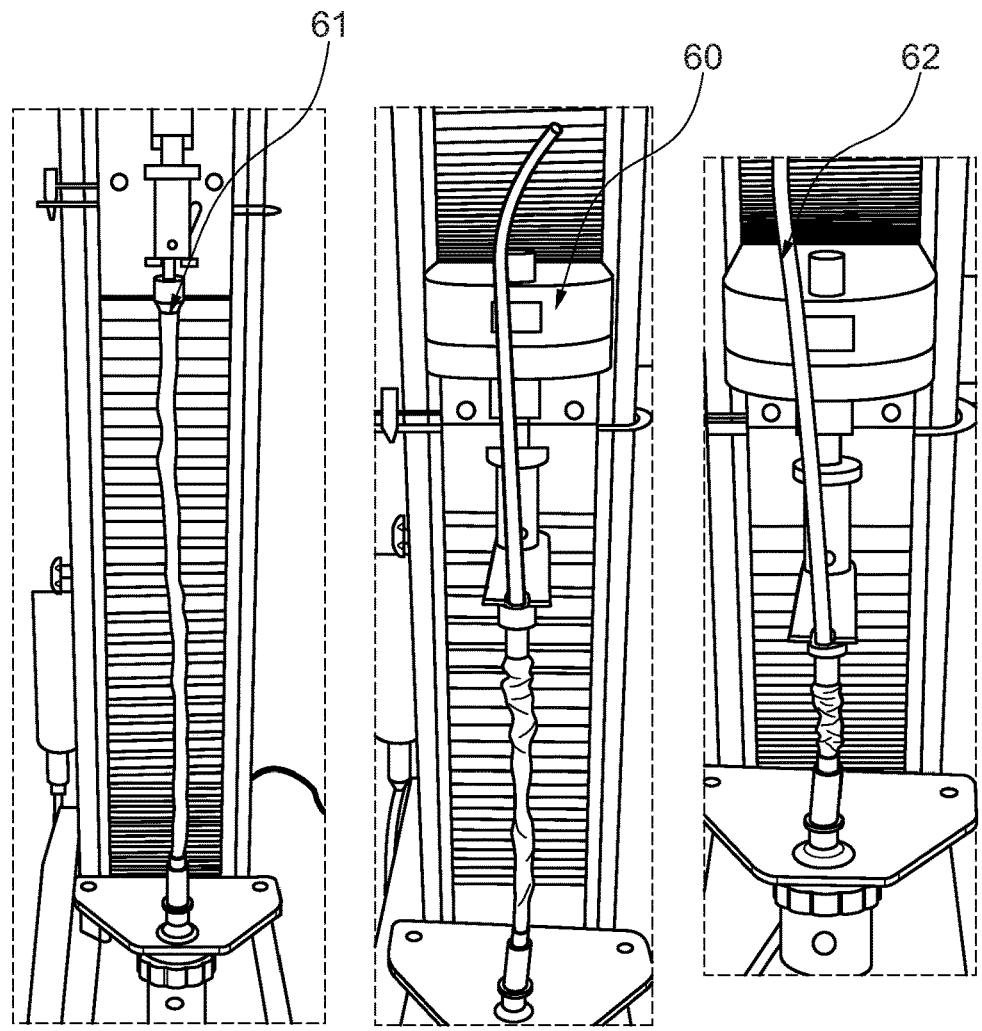
FIGS. 10A-10C illustrate a second inner package mounted in a test-rig for testing of collapse-force

FIGS. 10A, 10B and 10C illustrate testing of the collapse-force in three different points of the testing. FIG. 10A illustrates that the testing is ready to be performed, the second inner package 61 including the catheter is mounted in the test-rig 60. FIG. 10B illustrates the second inner package half-way through the test. FIG. 10C illustrates the second inner package at the finishing of the test, i.e. when 30 cm of the catheter 62 has been exposed.

EXAMPLES

The diffusion through materials follows Fick's law, as long as the material is under steady state, meaning that an equilibrium state has occurred between the material and the surroundings.

Fick's law states that the amount, M of material (e.g. water molecules) that flows through a cross-section of material, S of a barrier material over time, t is known as the flux, J:

$$J = \frac{\partial M}{S \cdot \partial t}$$

This equation can be re-written particularly with the purpose of gasses passing through a material:

$$R = \frac{D \cdot A \cdot p}{d}$$

In this equation, R is the diffusion rate (given in g/mm/time), D is a diffusion constant corresponding to the water vapour transmission rate (WVTR), A is the area over which diffusion occurs, p is the pressure difference (difference in RH) across the material, and d is the distance over which the diffusion may occur. This means that the barrier flow per day (BF) from a package including liquid given in mass per time unit can be calculated as follows:

$$BF = WVTR \cdot A \cdot p$$

WVTR should in this equation be given in g/(m²·24 h), the area A should be given in m² and p should be given as the % difference in relative humidity, RH.

In this disclosure, a double-package comprising a first outer package and a second inner package may be depicted.

The barrier flow (BF) through such a double-package is calculated using the following formula:

$$BF(\text{system}) = \frac{1}{\frac{1}{BF(\text{outer})} + \frac{1}{BF(\text{inner})}};$$

where BF(system) is the barrier flow through the double package, BF(outer) is the barrier flow through the outer package and BF(inner) is the barrier flow through the inner package. The barrier flow is measured in g/24 h.

Thus, if the barrier flow through each of the packages (the first outer package and the second inner package) is known, e.g. determined according to Fick's law, the barrier flow through the double package can be calculated using this formula.

One object of this invention is to keep the RH-value in the intermediate cavity between a second inner package and a first outer package below 90%. Using the above equations and understanding, the RH-value in this intermediate cavity can be calculated as follows:

$$RH(\text{cavity}) = RH(\text{storage}) + (100 - RH(\text{storage})) \cdot \frac{\frac{1}{BF(\text{outer})}}{\frac{1}{BF(\text{outer})} + \frac{1}{BF(\text{inner})}};$$

wherein BF(outer) is the barrier flow through the first outer package given in g/24 h, BF(inner) is the barrier flow through the second inner package given in g/24 h, RH(cavity) is the absolute RH-value in the intermediate cavity and RH(storage) is the absolute RH-value at the storage location external to the first outer package.

Figure 11:
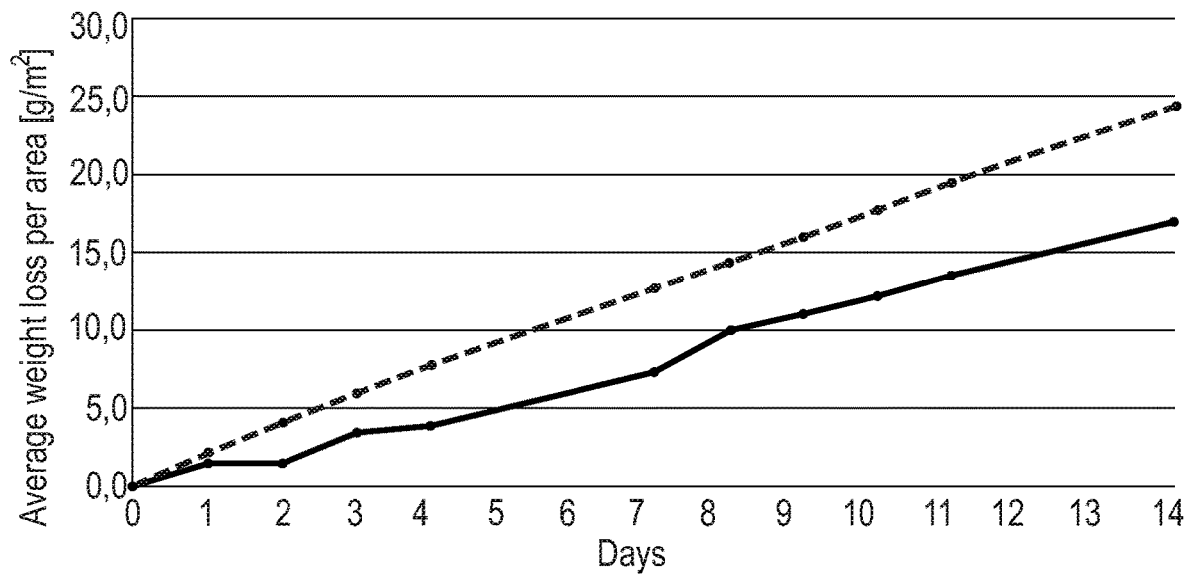
FIG. 11 illustrates weight loss per day as a result of evaporation through a material

The tests mentioned below are performed by determining the water vapour permeability (the barrier flow) through a material used for the second inner package using test method A described here. According to test method A, the water vapour permeability is determined by enclosing an amount of liquid in test-package made of a test-material and leaving this test-package in a conditioned environment, e.g. 65% RH, i.e. a difference between absolute RH value on either side of the test material of 65%, and 30° C. until the water vapour transmission per 24 h is steady. The test-package is made as illustrated in FIG. 5. The second inner package is made of a tubular material, which in a flattened condition has a width of 16.5 mm, corresponding to a diameter of approximately 10 mm. The water vapour transmission being steady is determined by weighing the test-packages once a day for a period of up to 2 weeks. In the first few days, there may be a situation where the test-packages are not in a steady state—therefore, weighing over at least 10 days but up to 2 weeks is preferred. Plotting the weight-loss per day clearly reveals when the steady state has occurred; an example can be seen in FIG. 11. In this figure, it is clear that the upper curve indicates a steady state having been reached within 1-2 days from initiation of test. The lower curve, on the other hand, indicates that it has taken 7 days before steady state having been reached. From this steady state and onwards, the slope on the curve corresponds to the barrier flow per 24 h measured in g/24 h. Dividing this with the area through which the flow occurs, provides a value for the water vapour transmission rate WVTR.

The RH-value in the intermediate cavity can be calculated as follows:

$$RH(\text{int}) = RH + (100 - RH) \cdot \frac{\frac{1}{BF(\text{outer})}}{\frac{1}{BF(\text{outer})} + \frac{1}{BF(\text{inner})}};$$

where RH(int) is the relative humidity value in the intermediate cavity in percentage, which in embodiments of this disclosure is below 90%. RH is the value of the relative humidity outside of the double package, BF(outer) is the barrier flow through the first outer package and BF(inner) is the barrier flow through the second inner package.

Test of Water Vapour Transmission Rate

The water vapour transmission rate was tested according to the methods described above. More particularly, the water vapour transmission rate for materials for the first outer package were tested according to ASTM F1249-13 at 90% RH and 38° C., and the water vapour transmission rate for materials for the second inner package were tested using test method A described above at 65% RH and 30° C. The following materials and obtained values are given below:

First Outer Package:

| ID | Material | WVTR-value (g/(m² · 24 h)) |
|---|---|---|
| 1a | PETP 12/PE 80 | 4.5 |
| 2a | OPA 12/PE 100 | 3.7 |
| 3a | PETP 12/PETP 12/PE 60 | 5.0 |
| 4a | PETP12/PETP 12/PE 60 | 5.3 |
| 5a | PETP 12/PETP 12/PE 65 | 2.1 |

Specimen ID 1a is a laminate material comprising an outer layer of PETP of a thickness of 12 μm and an inner layer of PE of a thickness of 80 μm.

Specimen ID 2a is a laminate material with an outer layer of OPA of 12 μm and an inner layer of PE of a thickness of 100 μm.

Specimen ID 3a is a laminate material with two layers of PETP of 12 μm each and an inner layer of PE of a thickness of 60 μm.

Specimen ID 4a is a laminate material with two layers of PETP of 12 μm each and an inner layer of PE of a thickness of 60 μm.

Specimen ID 5a is a laminate material with two layers of PETP of 12 μm each and an inner layer of PE of a thickness of 65 μm.

Second Inner Package:

| ID | Material | WVTR-value (g/(m² · 24 h)) |
|---|---|---|
| 1b | 5 layer film, PE + SIBS, 60 μm | 1.59 |
| 2b | PE 50 μm | 3.05 |
| 3b | 5 layer film, PE + SIBS, 70 μm | 1.47 |

Specimen ID 1b is a 5 layer film-material, where the three innermost layers are SIBS, and the outer layers are PE from the brand Queo® from Borealis. The total thickness is 60 μm.

Specimen ID 2b is a three-layer film-material of PE from the brand Queo® from Borealis.

Specimen ID 3b is a 5 layer film-material, where the innermost layer is SIBS, the layers covering this innermost layer are a blend of PE and SIBS of the brand Queo® from Borealis, and the outer layers are PE also from the brand Queo® from Borealis. The total thickness is 70 μm.

Figure 12:
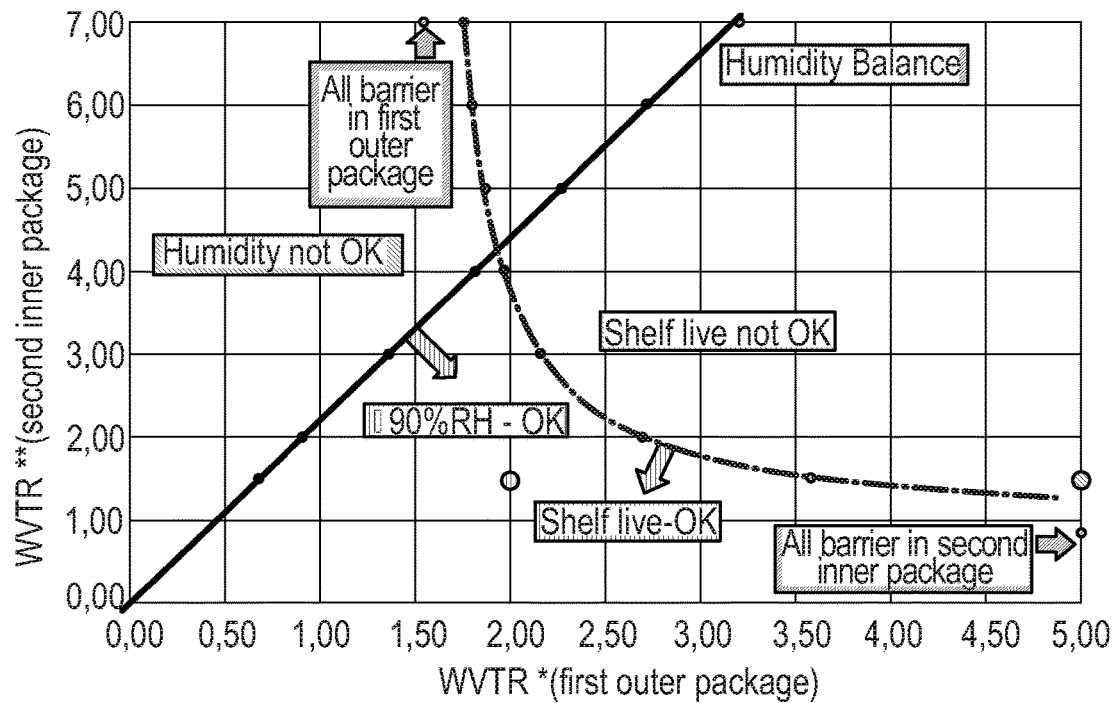
FIGS. 12 and 13 illustrate the balance between shelf life and the humidity level in a double package.

FIG. 12 illustrates the area between two curves that provides acceptable correspondence between WVTR values of the first outer package and WVTR values of the second inner package. The WVTR values are given in g/(m²·24 h). The WVTR values of the first outer package are measured according to ASTM F1249 at 38° C. and 90% RH, whereas the WVTR values of the second inner package are measured according to test method A as described above, at 30° C. and 65% RH. The linear curve sets the humidity condition, which is that the value of the relative humidity (RH) in the intermediate cavity between the inner surface of the first outer package and the outer surface of the second inner package, i.e. the absolute RH value inside the cavity, should be below 90%. The exponentially decreasing curve sets the shelf-life of the double package. The shelf-life is set to be at least 2 years, meaning that there should be liquid left in the package after two years. In the tests, it was depicted that 16 ml of liquid was included in the package and that half of this was allowed to evaporate over 2 years.

Towards the right is indicated the possibility of having the second inner package very close to completely water vapour impermeable—meaning that the second inner package provides the barrier for preventing liquid from evaporation from the second inner package. Towards the top is indicated the opposite situation, namely that first outer package provides the barrier for liquid evaporation. This situation, the first outer package provides the barrier, is not part of the embodiments of this disclosure. The embodiments of this disclosure are in the area between (under) the two curves indicated by the two arrows pointing in towards this area and the text "shelf-life ok" and "<90% RH ok". In FIG. 12, the first outer package has a surface area of approximately 37000 mm². The second inner package has a surface area of approximately 12000 mm². The green dot lying below the curves (at a WVTR value of 2 for the first outer package and 1.5 for the second inner package) indicates an example of packages falling within the scope of the embodiments of this disclosure. The red dot lying to the right and above the curve (at a WVTR value of 5 for the second inner package and 1.5 for the first outer package) indicates an example of a double package falling outside the scope of the embodiments of this disclosure.

The linear curve in FIG. 12 accordingly represents combinations of WVTR values for the second inner package and WVTR values for the first outer package which result in an absolute RH value inside the cavity of 90%. Thus, the slope of the linear curve in FIG. 12 represents a ratio between WVTR values for the second inner package and WVTR values for the first outer package, which result in an absolute RH value inside the cavity of exactly 90%, with the specified surface areas of the packages. Ratios of inner and outer WVTR values below the linear curve result in absolute RH values inside the intermediate cavity being below 90%. The 90%-RH ratio for the embodiment of FIG. 12 having the first outer package surface area of approximately 37000 mm² and second inner package surface area of approximately 12000 mm² is approximately 2.2, while the ratio between the surface area of the first outer package and second inner package is approximately 3.1. As seen above, the relative humidity in the intermediate cavity depends also on the surface area of the second inner and the first outer package. Taking account of this dependency may be achieved by dividing the 90%-RH ratio with the ratio between the surface area of the first outer package and second inner package, which yields a value of approximately 0.71. This value corresponds to a normalised 90%-RH ratio between WVTR values for the second inner package and WVTR values for the first outer package for which an intermediate cavity relative humidity of 90% taking into account the difference in surface areas of the second inner and the first outer package.

Figure 13:
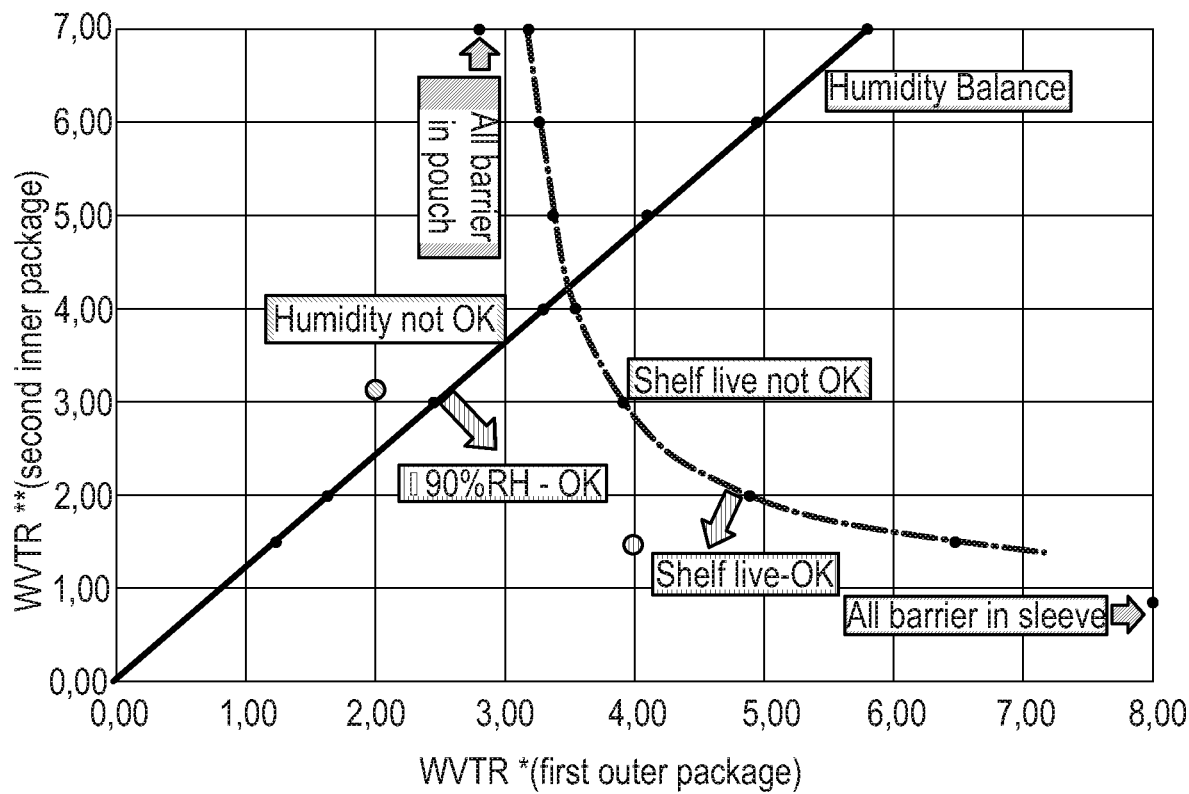

FIG. 13 illustrates another embodiment of a combination of a first outer package and a second inner package. In this embodiment, the first outer package is smaller than the one shown in FIG. 12. In FIG. 13, the first outer package has a surface area of approximately 20500 mm². Like in FIG. 12, the second inner package has a surface area of approximately 12000 mm². The green dot lying below the curves (at a WVTR value of 4 for the first outer package and 1.5 for the second inner package) indicates an example of packages falling within the scope of the embodiments of this disclosure. The red dot lying to the left and above the curves (at a WVTR value of 2 for the second inner package and above 3 for the first outer package) indicates an example of a double package falling outside the scope of the embodiments of this disclosure. The 90%-ratio, as defined above, for the FIG. 13 embodiment having a first outer package surface area of approximately 20500 mm² and a second inner package surface area of approximately 12000 mm² is approximately 1.2, while the ratio between the surface area of the first outer package and second inner package is approximately 1.7. Again, dividing the 90%-RH ratio with the ratio between the surface area of the first outer package and second inner package may be done in order to take into account the difference in surface areas of the first outer and the second inner package, and yields the same value of approximately 0.71 as for the embodiment illustrated in FIG. 12. Accordingly, the normalised 90%-RH ratio is the same for the embodiment of FIG. 12 and the embodiment of FIG. 13, confirming that the normalised 90%-RH ratio indeed takes into account the difference in surface areas of the first inner and the second outer packages.

EXAMPLES

Referring to the tables above, the specimen IDs in the tables and FIGS. 12 and 13, examples of combinations of first outer packages and second inner packages are given below.

Example 1

The first outer package is made of a material corresponding to specimen 2a with a WVTR value of 3.7 g/(m²·24 h) and the second inner package is made of a material corresponding to specimen 3b with a WVTR-value of 1.47 g/(m²·24 h). The first outer package has a surface area of 37000 mm² and the second inner package has a surface area of approximately 12000 mm², corresponding to the curves illustrated in FIG. 12. The example is indicated in FIG. 12. This example will provide a catheter assembly having a balanced diffusion through the first outer package, so that the relative humidity (RH) in the intermediate cavity, i.e. the absolute RH value inside the intermediate cavity, is below 90%. Furthermore, the shelf life for such an assembly will also be okay, because the crossing between the lines indicating the WVTR of 3.7 g/(m²·24 h) for the first outer package and 1.47 g/(m²·24 h) for the second inner package is below the exponential curve for the shelf-life.

Example 2

The first outer package is made of a material corresponding to specimen 5a with a WVTR value of 2.1 g/(m²·24 h) and the second inner package is made of a material corresponding to specimen 1b with a WVTR-value of 1.59 g/(m²·24 h). The first outer package has a surface area of 37000 mm² and the second inner package has a surface area of approximately 12000 mm², corresponding to the curves illustrated in FIG. 12. The example is indicated in FIG. 12. This example will provide a catheter assembly having a balanced diffusion through the first outer package, so that the relative humidity (RH) in the intermediate cavity, i.e. the absolute RH value inside the intermediate cavity, is below 90%. Furthermore, the shelf life for such an assembly will also be okay, because the crossing between the lines indicating the WVTR of 2.1 g/(m²·24 h) for the first outer package and 1.59 g/(m²·24 h) for the second inner package is below the exponential curve for the shelf-life.

Example 3

The first outer package is made of a material corresponding to specimen 5a with a WVTR value of 2.1 g/(m²·24 h) and the second inner package is made of a material corresponding to specimen 2b with a WVTR-value of 3.05 g/(m²·24 h). The first outer package has a surface area of 37000 mm² and the second inner package has a surface area of approximately 12000 mm², corresponding to the curves illustrated in FIG. 12. The example is indicated in FIG. 12. This example will provide a catheter assembly having a balanced diffusion through the first outer package, so that the relative humidity (RH) in the intermediate cavity, i.e. the absolute RH value inside the intermediate cavity, is below 90%. Furthermore, the shelf life for such an assembly will also be okay, because the crossing between the lines indicating the WVTR of 2.1 g/(m²·24 h) for the first outer package and 3.05 g/(m²·24 h) for the second inner package is below the exponential curve for the shelf-life.

Example 4

The first outer package is made of a material corresponding to specimen 5a with a WVTR value of 2.1 g/(m²·24 h) and the second inner package is made of a material corresponding to specimen 3b with a WVTR-value of 1.47 g/(m²·24 h). The first outer package has a surface area of 37000 mm² and the second inner package has a surface area of approximately 12000 mm², corresponding to the curves illustrated in FIG. 12. The example is indicated in FIG. 12. This example will provide a catheter assembly having a balanced diffusion through the first outer package, so that the relative humidity (RH) in the intermediate cavity, i.e. the absolute RH value inside the intermediate cavity, is below 90%. Furthermore, the shelf life for such an assembly will also be okay, because the crossing between the lines indicating the WVTR of 2.1 g/(m²·24 h) for the first outer package and 1.47 g/(m²·24 h) for the second inner package is below the exponential curve for the shelf-life.

Example 5

The first outer package is made of a material corresponding to specimen 1a with a WVTR value of 4.5 g/(m²·24 h) and the second inner package is made of a material corresponding to specimen 1b with a WVTR-value of 1.59 g/(m²·24 h). The first outer package has a surface area of 20500 mm² and the second inner package has a surface area of approximately 12000 mm², corresponding to the curves illustrated in FIG. 13. The example is indicated in FIG. 13. This example will provide a catheter assembly having a balanced diffusion through the first outer package, so that the relative humidity (RH) in the intermediate cavity, i.e. the absolute RH value inside the intermediate cavity, is below 90%. Furthermore, the shelf life for such an assembly will also be okay, because the crossing between the lines indicating the WVTR of 4.5 g/(m²·24 h) for the first outer package and 1.59 g/(m²·24 h) for the second inner package is below the exponential curve for the shelf-life.

Example 6

The first outer package is made of a material corresponding to specimen 2a with a WVTR value of 3.7 g/(m²·24 h) and the second inner package is made of a material corresponding to specimen 1b with a WVTR-value of 1.59 g/(m²·24 h). The first outer package has a surface area of 20500 mm² and the second inner package has a surface area of approximately 12000 mm², corresponding to the curves illustrated in FIG. 13. The example is indicated in FIG. 13. This example will provide a catheter assembly having a balanced diffusion through the first outer package, so that the relative humidity (RH) in the intermediate cavity, i.e. the absolute RH value inside the intermediate cavity, is below 90%. Furthermore, the shelf life for such an assembly will also be okay, because the crossing between the lines indicating the WVTR of 3.7 g/(m²·24 h) for the first outer package and 1.59 g/(m²·24 h) for the second inner package is below the exponential curve for the shelf-life.

Example 7

The first outer package is made of a material corresponding to specimen 3a with a WVTR value of 5.0 g/(m²·24 h) and the second inner package is made of a material corresponding to specimen 1b with a WVTR-value of 1.59 g/(m²·24 h). The first outer package has a surface area of 20500 mm² and the second inner package has a surface area of approximately 12000 mm², corresponding to the curves illustrated in FIG. 13. The example is indicated in FIG. 13. This example will provide a catheter assembly having a balanced diffusion through the first outer package, so that the relative humidity (RH) in the intermediate cavity, i.e. the absolute RH value inside the intermediate cavity, is below 90%. Furthermore, the shelf life for such an assembly will also be okay, because the crossing between the lines indicating the WVTR of 5.0 g/(m²·24 h) for the first outer package and 1.59 g/(m²·24 h) for the second inner package is below the exponential curve for the shelf-life.

Example 8

The first outer package is made of a material corresponding to specimen 4a with a WVTR value of 5.3 g/(m²·24 h) and the second inner package is made of a material corresponding to specimen 1b with a WVTR-value of 1.59 g/(m²·24 h). The first outer package has a surface area of 20500 mm² and the second inner package has a surface area of approximately 12000 mm², corresponding to the curves illustrated in FIG. 13. The example is indicated in FIG. 13. This example will provide a catheter assembly having a balanced diffusion through the first outer package, so that the relative humidity (RH) in the intermediate cavity, i.e. the absolute RH value inside the intermediate cavity, is below 90%. Furthermore, the shelf life for such an assembly will also be okay, because the crossing between the lines indicating the WVTR of 5.3 g/(m²·24 h) for the first outer package and 1.59 g/(m²·24 h) for the second inner package is below the exponential curve for the shelf-life.

Example 9

The first outer package is made of a material corresponding to specimen 5a with a WVTR value of 2.1 g/(m²·24 h) and the second inner package is made of a material corresponding to specimen 1b with a WVTR-value of 1.59 g/(m²·24 h). The first outer package has a surface area of 20500 mm² and the second inner package has a surface area of approximately 12000 mm², corresponding to the curves illustrated in FIG. 13. The example is indicated in FIG. 13. This example will provide a catheter assembly having a balanced diffusion through the first outer package, so that the relative humidity (RH) in the intermediate cavity, i.e. the absolute RH value inside the intermediate cavity, is below 90%. Furthermore, the shelf life for such an assembly will also be okay, because the crossing between the lines indicating the WVTR of 2.1 g/(m²·24 h) for the first outer package and 1.59 g/(m²·24 h) for the second inner package is below the exponential curve for the shelf-life.

Example 10

The first outer package is made of a material corresponding to specimen 2a with a WVTR value of 3.7 g/(m²·24 h) and the second inner package is made of a material corresponding to specimen 2b with a WVTR-value of 3.05 g/(m²·24 h). The first outer package has a surface area of 20500 mm² and the second inner package has a surface area of approximately 12000 mm², corresponding to the curves illustrated in FIG. 13. The example is indicated in FIG. 13. This example will provide a catheter assembly having a balanced diffusion through the first outer package, so that the relative humidity (RH) in the intermediate cavity, i.e. the absolute RH value inside the intermediate cavity, is below 90%. Furthermore, the shelf life for such an assembly will also be okay, because the crossing between the lines indicating the WVTR of 3.7 g/(m²·24 h) for the first outer package and 3.05 g/(m²·24 h) for the second inner package is below the exponential curve for the shelf-life.

Examples 11-15

In these examples, the second inner package is made of a material corresponding to specimen 3b with a WVTR value of 1.47 g/(m²·24 h). The first outer package has a surface area of 20500 mm² and the second inner package has a surface area of approximately 12000 mm², corresponding to the curves illustrated in FIG. 13.

The variation between the examples 11-15 is in the material of the first outer package, which varies from specimen 1a to 5a. It is clear from FIG. 13 that all of these examples fulfil the requirements with respect to relative humidity and shelf-life, because the intersections between the curve indicating a second inner package with a WVTR value of 1.47 and the WVTR values of specimens 1a to 5a all are positioned below the exponential curve of the shelf-life and to the right of the curve indicating RH below 90%.

COMPARATIVE EXAMPLES

The first outer package is made of a material corresponding to specimen 1a with a WVTR value of 4.5 g/(m²·24 h) and the second inner package is made of a material corresponding to specimen 1b with a WVTR-value of 1.59 g/(m²·24 h). The first outer package has a surface area of 37000 mm² and the second inner package has a surface area of approximately 12000 mm², corresponding to the curves illustrated in FIG. 12. This example will provide a catheter assembly having a balanced diffusion through the first outer package, so that the relative humidity (RH) in the intermediate cavity, i.e. the absolute RH value inside the intermediate cavity, is below 90%. However, the shelf-life will not fulfil the requirement of two years, because too much liquid will evaporate. This is clear from FIG. 12, because the cross-point between 4.5 on the X-axis and 1.59 on the Y-axis will be above the exponential curve of the shelf-life.

It is further clear from FIG. 12 that combining a first outer package of a material corresponding to specimens 3a or 4a having a WVTR value that is higher than specimen 1a with a second inner package of a material corresponding to specimen 1b (with a WVTR value of 1.59 g/(m²·24 h)) will lead to assemblies having a shelf life that is not acceptable. As mentioned above, the cross points between 5.0 and 1.59 and 5.3 and 1.59 will be above the exponential curve indicating the acceptable shelf-life.

In another comparative example, the first outer package is made of a material corresponding to specimen 1a with a WVTR value of 4.5 g/(m²·24 h) and the second inner package is made of a material corresponding to specimen 2b with a WVTR-value of 3.05 g/(m²·24 h). The first outer package has a surface area of 20500 mm² and the second inner package has a surface area of approximately 12000 mm², corresponding to the curves illustrated in FIG. 13. This example will provide a catheter assembly having a balanced diffusion through the first outer package, so that the relative humidity (RH) in the intermediate cavity, i.e. the absolute RH value inside the intermediate cavity, is below 90%. However, the shelf-life will not fulfil the requirement of two years, because too much liquid will evaporate. This is clear from FIG. 13, because the cross-point between 4.5 on the X-axis and 3.05 on the Y-axis will be above the exponential curve of the shelf-life.

It is further clear from FIG. 13 that combining a first outer package of a material corresponding to specimens 3a or 4a having a WVTR value that is higher than specimen 1a with a second inner package of a material corresponding to specimen 1b (with a WVTR value of 3.05 g/(m²·24 h)) will lead to assemblies having a shelf life that is not acceptable. As mentioned above, the cross points between 5.0 and 3.05 and 5.3 and 3.05 will be above the exponential curve indicating the acceptable shelf-life.

In a further comparative example, the first outer package is made of a material corresponding to specimen 5a with a WVTR value of 2.1 g/(m²·24 h) and the second inner package is made of a material corresponding to specimen 2b with a WVTR-value of 3.05 g/(m²·24 h). The first outer package has a surface area of 20500 mm² and the second inner package has a surface area of approximately 12000 mm², corresponding to the curves illustrated in FIG. 13. This example will provide a catheter assembly having a too low diffusion, meaning that the relative humidity (RH) in the intermediate cavity is above 90%. The shelf-life will fulfil the requirement of two years. This is clear from FIG. 13, because the cross-point between 2.1 on the X-axis and 3.05 on the Y-axis will be above the curve indicating the RH-level of 90%. This means that for such an assembly, there is a risk that the condensed liquid inside the intermediate cavity will not evaporate and therefore the second inner package may have a wet surface so that it is not as easy to handle.

Test of Collapse-Force

The collapse-force was tested in accordance with test method B as described below. The collapse-force was tested on test-specimens of second inner package, where the second inner package is in the form of a sleeve as illustrated for example in FIGS. 3, 4 and 8. In the fully extended state of the sleeve, prior to the test being performed, the sleeve had a length of approximately 340 mm, corresponding to the length of a sleeve applied to a male catheter. The equipment used was an Instron tensile tester. For further reference, see FIGS. 9 and 10. Test method B includes the following steps:
1. Place the catheter with the second inner package on a supporting bar with the connector in contact with the supporting bar.
2. Move the upper fixture down, so the lower end of the fixture, is in the middle of the lowest (the distal) eyelet.
3. Make a zero point setting on the equipment (with the upper fixture, but without the catheter touching the upper fixture).
4. Start the test. The upper fixture is now moving down. The sleeve is being pushed down, while the catheter is not moving.
5. Note the compression load after 300 mm.

The compression load corresponds to the collapse-force and is noted in N.

The table below gives examples of collapse-forces tested:

| ID | Material | Collapse-force (N) |
| --- | --- | --- |
| 1c | PE/SIBS multilayer film | 2.97N |
| 2c | PE 28 µm | 2.4N |
| 3c | PE 50 µm | 2.92 |
| 4c | PE/SIBS multilayer film, 60 µm | 2.11 |
| 5c | PE/SIBS multilayer film 80 µm | 10.13N |
| 6c | PE/SIBS multilayer film 80 µm | 12.73N |

Specimen ID 1c is a 5 layer film-material, where the innermost layer is SIBS, the layers covering this innermost layer are a blend of PE and SIBS of the brand Queo® from Borealis, and the outer layers are PE also from the brand Queo® from Borealis. The total thickness is 70 µm. This corresponds to specimen 3b above.

Specimen ID 2c is a one-layer film-material of PE from the brand Queo® from Borealis.

Specimen ID 3c is a three-layer film-material of PE from the brand Queo® from Borealis. This corresponds to specimen 2b above.

Specimen ID 4c is a 5 layer film-material, where the three innermost layers are SIBS, and the outer layers are PE from the brand Queo® from Borealis. The total thickness is 60 µm. This corresponds to specimen 1b above.

Specimen ID 5c is a 5 layer film-material, where three innermost layers are a blend of PE and SIBS of the brand Queo® from Borealis, and the outer layers are PE from the brand Eltex. The total thickness is 80 µm.

Specimen ID 6c is a 5 layer film-material, where the three innermost layers are a blend of PE and SIBS of the brand Eltex® from Ineos, and the outer layers are PE also from the brand Eltex® from Ineos. The total thickness is 80 µm.

The tests illustrate that specimens 1c, 2c, 3c and 4c all have a collapse-force, measured according to test method B as described above, which is below 3 N. This means that all of these sleeves are easily collapsible to the extent that even users having very poor hand dexterity will find them very easy to handle, due to the low collapse-force. Specimens 5c and 6c on the other hand, have a quite high collapse-force—and will thus be more difficult to collapse for users having poor hand dexterity.

EMBODIMENTS

1. A urinary catheter assembly comprising a first outer package of a first material, the outer package contains a second inner package of a second material, an intermediate cavity defined as an area inside the first outer package and outside the second inner package, the second inner package defining an enclosure, the enclosure containing an intermittent urinary catheter with a hydrophilic coating and a swelling medium, wherein the permeability of the outer package and the inner package is balanced in such a way that the RH value is below 90% in the intermediate cavity.

2. A urinary catheter assembly comprising a first outer package of a first material, the first material having a first water vapour transmission rate (WVTR), the first outer package contains a second inner package of a second material, the second material having a second water vapour transmission rate (WVTR);

an intermediate cavity defined as an area inside the first outer package and outside the second inner package, the second inner package defining an enclosure, the enclosure containing an intermittent urinary catheter with a hydrophilic coating, and a swelling medium;

wherein the relationship between the first and second water vapour transmissions are such that they fulfil the following equations:

$$BF(\text{outer}) = WVTR(\text{outer}) \cdot A(\text{outer}) \cdot p$$

$$BF(\text{inner}) = WVTR(\text{inner}) \cdot A(\text{inner}) \cdot p$$

$$RH(\text{cavity}) =$$

$$RH(\text{storage}) + (100 - RH(\text{storage})) \cdot \frac{\frac{1}{BF(\text{outer})}}{\frac{1}{BF(\text{outer})} + \frac{1}{BF(\text{inner})}} < 90\%;$$

wherein BF(outer) is the barrier flow through the first outer package given in g/24 h, BF(inner) is the barrier flow through the second inner package given in g/24 h, WVTR (outer) is the first water vapour transmission rate and WVTR (inner) is the second water vapour transmission rate, A(inner) is the surface area of the first outer package, A(outer) is the surface area of the second inner package and p is the difference in RH value between the ambience and the inside of the package.

3. A urinary catheter assembly comprising a first outer package of a first material, the first material having a first water vapour transmission rate (WVTR), the first outer package contains a second inner package of a second material, the second material having a second water vapour transmission rate (WVTR);

an intermediate cavity defined as an area inside the first outer package and outside the second inner package, the second inner package defining an enclosure, the enclosure containing an intermittent urinary catheter with a hydrophilic coating, and a swelling medium;

wherein the relationship between the first and second water vapour transmissions are such that they fulfil the following equations:

$$BF(\text{outer}) = WVTR(\text{outer}) \cdot A(\text{outer}) \cdot p(\text{outer})$$

$$BF(\text{inner}) = WVTR(\text{inner}) \cdot A(\text{inner}) \cdot p(\text{inner})$$

$$RH(\text{cavity}) =$$

$$RH(\text{storage}) + (100 - RH(\text{storage})) \cdot \frac{\frac{1}{BF(\text{outer})}}{\frac{1}{BF(\text{outer})} + \frac{1}{BF(\text{inner})}} < 90\%;$$

wherein BF(outer) is the barrier flow through the first outer package given in g/24 h, BF(inner) is the barrier flow through the second inner package given in g/24 h, WVTR (outer) is the first water vapour transmission rate and WVTR (inner) is the second water vapour transmission rate, A(inner) is the surface area of the first outer package, A(outer) is the surface area of the second inner package, p(outer) is the difference in RH-value between the ambience and the intermediate cavity, p(inner) is the difference in RH-value between the second inner package and the intermediate cavity, RH(cavity) is the RH-value in the intermediate cavity and RH(storage) is the RH-value at the storage location external to the first outer package.

4. A urinary catheter assembly comprising a first outer package of a first material, the first material having a first water vapour transmission rate (WVTR) measured according to ASTM F1249 at 90% RH and 38° C. between 1 g/(m$^2$·24 h) and 6 g/(m$^2$·24 h), the first outer package contains a second inner package of a second material, the second material having a second water vapour transmission rate (WVTR) measured according to test method A as described herein at 65% RH and 30° C. below 3 g/(m$^2$·24 h);

an intermediate cavity defined as an area inside the first outer package and outside the second inner package, the second inner package defining an enclosure, the enclosure containing an intermittent urinary catheter with a hydrophilic coating, and a swelling medium;

wherein the first water vapour transmission rate and the second water vapour transmission rate are balanced in such a way that the relative humidity (RH) value is below 90% in the intermediate cavity 5. A urinary catheter assembly comprising a first outer package (20) of a first material, the first material having a first water vapour transmission rate (WVTR) measured according to ASTM F1249 at 90% RH and 38° C. between 1 g/(m$^2$·24 h) and 6 g/(m$^2$·24 h), the first outer package (20) contains a second inner package (1) of a second material, the second material having a second water vapour transmission rate (WVTR) measured according to test method A as described herein at 65% RH and 30° C. below 3 g/(m$^2$·24 h);

an intermediate cavity (22, 25) defined as an area inside the first outer package (20) and outside the second inner package (1), the second inner package (1) defining an enclosure (21, 24), the enclosure (21, 24) containing an intermittent urinary catheter (2) with a hydrophilic coating, and a swelling medium;

wherein the first water vapour transmission rate and the second water vapour transmission rate are balanced in such a way that the relative humidity (RH) value is below 90% in the intermediate cavity (22, 25) and wherein the second inner package (1) is made of a multilayer film material comprising layers of Polyethylene (PE) and layers of Styrene-IsoButylene-Styrene (SIBS) and/or layers of combinations of PE and SIBS.

6. A urinary catheter assembly comprising a first outer package (20) of a first material, the first material having a first water vapour transmission rate (WVTR) measured according to ASTM F1249 at 90% RH and 38° C. between 1 g/(m$^2$·24 h) and 6 g/(m$^2$·24 h), the first outer package (20) contains a second inner package (1) of a second material, the second material having a second water vapour transmission rate (WVTR) measured according to test method A as described herein at 65% RH and 30° C. below 3 g/(m$^2$·24 h);

an intermediate cavity (22, 25) defined as an area inside the first outer package (20) and outside the second inner package (1), the second inner package (1) defining an enclosure (21, 24), the enclosure (21, 24) containing an intermittent urinary catheter (2) with a hydrophilic coating, and a swelling medium;

wherein the second inner package (1) comprises a tubular film element (7), which has a collapse-force measured according to test method B as described herein, being no larger than 6 N.

7. The intermittent urinary catheter assembly according to any of the preceding embodiments, wherein the first outer package has a first water vapour transmission rate measured as described here at 65% RH and 30° C. above 3 g/(m$^2$·24 h).

8. The intermittent urinary catheter assembly according to any of the preceding embodiments, wherein the second inner package has a second water vapour transmission rate measured according to test method A as described herein at 65% RH and 30° C. below 2 g/(m$^2$·24 h).

9. The intermittent urinary catheter assembly according to any of the preceding embodiments, wherein the second inner package is of tubular form and provides a close-fit about the catheter.

10. The intermittent urinary catheter assembly according to any of the preceding embodiments, wherein the second inner package has a diameter of 20 mm, but may be less such as 16 mm, 12 mm or 10 mm or even 9 mm.

11. The intermittent urinary catheter assembly according to any of the preceding embodiments, wherein the second inner package is closed with a first closure in the proximal end.

12. The intermittent urinary catheter assembly according to any of the preceding embodiments, wherein the second inner package is closed with a second closure in the distal end.

13. The intermittent urinary catheter assembly according to any of the preceding embodiments, wherein the first closure is a plug.

14. The intermittent urinary catheter assembly according to any of the preceding embodiments, wherein the second closure is a plug.

15. The intermittent urinary catheter assembly according to any of the preceding embodiments, wherein the first closure is a peel-welded closure.

16. The intermittent urinary catheter assembly according to any of the preceding embodiments, wherein the second closure is a peel-welded closure 17. The intermittent urinary catheter assembly according to any of the preceding embodiments, wherein the RH value in the intermediate cavity is below 85%.

18. The intermittent urinary catheter assembly according to any of the preceding embodiments, wherein the RH value in the intermediate cavity is below 80%.

19. The intermittent urinary catheter assembly according to any of the preceding embodiments, wherein the first outer package is made of a film-material.

20. The intermittent urinary catheter assembly according to any of the preceding embodiments, wherein the first outer package is made of a film-material and is welded for providing an enclosure.

21. The intermittent urinary catheter assembly according to any of the preceding embodiments, wherein the first outer package is made of a multiple layer film material of a laminate of PETP and PE.

22. The intermittent urinary catheter assembly according to any of the preceding embodiments, wherein the second inner package is made of a multiple layer film material of a laminate of PETP, PE and SIBS.

23. The intermittent urinary catheter assembly according to any of the preceding embodiments, wherein the second inner package is useable as an insertion aid.

24. The intermittent urinary catheter assembly according to any of the preceding embodiments, wherein the second inner package has a collapsibility such that the force used to compress the inner package to expose 30 cm is below 6 N.

25. The intermittent urinary catheter assembly according to any of the preceding embodiments, wherein the first outer package is made of a film-material with a thickness below 200 μm.

26. The intermittent urinary catheter assembly according to any of the preceding embodiments, wherein the first outer package is made of a multilayer film-material with a thickness below 200 μm.

27. The intermittent urinary catheter assembly according to any of the preceding embodiments, wherein the second inner package is made of a film-material with a thickness below 200 μm.

28. The intermittent urinary catheter assembly according to any of the preceding embodiments, wherein the second inner package is made of a multilayer film-material with a thickness below 200 μm.

29. The intermittent urinary catheter assembly according to any of the preceding embodiments, wherein the tip portion is a flex tip.

30. A urinary catheter assembly according to any of the preceding embodiments, wherein the second inner package comprises a tubular film element, which is easily collapsible to an extent where at least 30 cm from the proximal end of a male catheter can be exposed without noticeable resistance.

The invention claimed is:

1. A urinary catheter assembly comprising,
a first outer package comprising a first material, the first material having a first water vapour transmission rate (WVTR) measured according to ASTM F1249 at 90% relative humidity (RH) and 38° C. between 1 g/(m2·24 h) and 6 g/(m2·24 h);
a second inner package contained inside of the first outer package, the second inner package comprising a second material, the second material having a second WVTR measured according to test method A at 65% RH and 30° C. below 3 g/(m2·24 h); and
an intermediate cavity defined as an area inside the first outer package and outside the second inner package;
wherein the second inner package defines an enclosure containing a swelling medium and an intermittent urinary catheter comprising a hydrophilic coating.

2. The urinary catheter assembly according to claim 1, wherein the first water vapour transmission rate and the second water vapour transmission rate are balanced to adapt a relative humidity value in the intermediate cavity below 90%.

3. The urinary catheter assembly according to claim 1, wherein the second inner package is made of a multilayer film material comprising layers of Polyethylene and layers of Styrene-IsoButylene-Styrene.

4. The urinary catheter assembly according to claim 1, wherein the first outer package defines a first outer package surface area, the second inner package defines a second inner package surface area, a surface area ratio is defined as the second inner package surface area divided by the first outer package surface area, a WVTR ratio is defined as the second WVTR divided by the first WVTR, and wherein the WVTR ratio is no larger than 0.7 times the surface area ratio.

5. The urinary catheter assembly according to claim 4, wherein the WVTR ratio is no larger than 0.6 times the surface area ratio.

6. The urinary catheter assembly according to claim 1, wherein the first outer package is comprises a film-material defining a perimeter edge, and the film-material is welded along the perimeter edge.

7. The urinary catheter assembly according to claim 1, wherein the second inner package is tubular.

8. The urinary catheter assembly according to claim 1, wherein the intermittent urinary catheter comprises an insertion tip and the second inner package comprises:
a handle slidingly disposed on the intermittent urinary catheter;
a tubular film element having a proximal end attached to the handle, wherein the tubular film element is configured to cover the intermittent urinary catheter and form an outlet for the insertion tip when the insertion tip is in an extended configuration; and
a connector attached to a distal end of the tubular film element, with the connector providing at the outlet communication with a lumen of the intermittent urinary catheter;
wherein the handle is attachable to the connector.

9. The urinary catheter assembly according to claim 8, wherein the connector and the handle are configured to be attached to each other in a detachable manner, so that when the connector and the handle are attached to each other, the intermittent urinary catheter is encapsulated completely inside the enclosure that is formed by the tubular film element, the handle, and the connector.

10. The urinary catheter assembly according to claim 8, further comprising:
a first closure in a proximal end of the tubular film element and a second closure in a distal end of the tubular film element.

11. The urinary catheter assembly according to claim 1, wherein the first outer package comprises a multiple layer film material of a laminate of Polyethylene terephthalate (PETP) and Polyethylene (PE).

12. The urinary catheter assembly according to claim 1, wherein the second inner package comprises a 5 layer film-material comprising a Styrene-IsoButylene-Styrene layer in a middle of the 5 layer film-material, with opposing outer layers of the 5 layer film-material comprising PE.

13. The urinary catheter assembly according to claim 1, wherein the second inner package comprises a sliding handle that is useable as an insertion aid.

14. The urinary catheter assembly according to claim 1, wherein the second inner package comprises a tubular film element (7) having a collapse-force; measured according to test method B of no larger than 6 N.

15. The urinary catheter assembly according to claim 14, wherein the tubular film element has a collapse-force no larger than 3 N.

16. The urinary catheter assembly according to claim 1, wherein the second inner package is provided in an annular closed-loop configuration contained inside the first outer package; and
wherein the first WVTR value of the first outer package is between 1 g/(m2·24 h) and 3 g/(m2·24 h) measured according to ASTM F1249 at 38° C. and 90% RH.

17. The urinary catheter assembly according to claim 1, wherein the second inner package is provided in rolled-up configuration with two convolutions and contained inside the first outer package; and
wherein the first WVTR value of the first outer package is between 4 g/(m2·24 h) and 6 g/(m2·24 h) measured according to ASTM F1249 at 38° C. and 90% RH.

* * * * *